(12) United States Patent
Handique et al.

(10) Patent No.: US 7,731,906 B2
(45) Date of Patent: Jun. 8, 2010

(54) PROCESSING PARTICLE-CONTAINING SAMPLES

(75) Inventors: Kalyan Handique, Ypsilanti, MI (US); Gene Parunak, Saline, MI (US); Aaron Kehrer, Ypsilanti, MI (US); Betty Wu, Canton, MI (US); Karthik Ganesan, Ann Arbor, MI (US)

(73) Assignee: HandyLab, Inc., Ann Arbor, MI (US)

( * ) Notice: Subject to any disclaimer, the term of this patent is extended or adjusted under 35 U.S.C. 154(b) by 540 days.

(21) Appl. No.: 10/567,002

(22) PCT Filed: Aug. 2, 2004

(86) PCT No.: PCT/US2004/025181

§ 371 (c)(1),
(2), (4) Date: Jan. 31, 2006

(87) PCT Pub. No.: WO2005/011867

PCT Pub. Date: Feb. 10, 2005

(65) Prior Publication Data

US 2006/0205085 A1     Sep. 14, 2006

Related U.S. Application Data

(60) Provisional application No. 60/491,269, filed on Jul. 31, 2003, provisional application No. 60/551,785, filed on Mar. 11, 2004, provisional application No. 60/553,553, filed on Mar. 17, 2004.

(51) Int. Cl.
*B01L 3/02* (2006.01)

(52) U.S. Cl. ...................................... 422/100

(58) Field of Classification Search .................. 422/100
See application file for complete search history.

(56) References Cited

U.S. PATENT DOCUMENTS 1,616,419 A     2/1927    Wilson (Continued)

FOREIGN PATENT DOCUMENTS

WO       WO 99/09042      2/1999

(Continued)

OTHER PUBLICATIONS

Brody, et al., "Diffusion-based extraction in a microfabricated device" *Sensors and Actuators (Elsevier)*, vol. A58, No. 1: pp. 13-18 (1997).

(Continued)

*Primary Examiner*—Walter D Griffin
*Assistant Examiner*—Bobby Ramdhanie
(74) *Attorney, Agent, or Firm*—Knobbe Martens Olson & Bear LLP

(57) ABSTRACT

A microfluidic device includes an input port for inputting a particle-containing liquidic samples into the device, a retention member, and a pressure actuator. The retention member is in communication with the input port and is configured to spatially separate particles of the particle-containing liquidic sample from a first portion of the liquid of the particle containing fluidic sample. The pressure actuator recombines at least some of the separated particles with a subset of the first portion of the liquid separated from the particles. The device can also include a lysing chamber that receives the particles and liquid from the retention member. The lysing chamber thermally lyses the particles to release contents thereof.

5 Claims, 13 Drawing Sheets

U.S. PATENT DOCUMENTS

| | | |
|---|---|---|
| 1,773,401 A | 8/1930 | Lovekin |
| 3,528,449 A | 9/1970 | Witte et al. |
| 4,139,005 A | 2/1979 | Dickey |
| 4,612,959 A | 9/1986 | Costello |
| 4,654,127 A | 3/1987 | Baker et al. |
| 4,673,657 A | 6/1987 | Christian |
| 4,946,562 A | 8/1990 | Guruswamy et al. |
| 4,949,742 A | 8/1990 | Rando et al. |
| 4,963,498 A | 10/1990 | Hillman et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,053,199 A | 10/1991 | Keiser et al. |
| 5,061,336 A | 10/1991 | Soane |
| 5,064,618 A | 11/1991 | Baker et al. |
| 5,071,531 A | 12/1991 | Soane |
| 5,126,002 A | 6/1992 | Iwata et al. |
| 5,126,022 A | 6/1992 | Soane et al. |
| 5,135,627 A | 8/1992 | Soane |
| 5,135,872 A | 8/1992 | Pouletty et al. |
| 5,147,606 A | 9/1992 | Charlton et al. |
| 5,208,163 A | 5/1993 | Charlton et al. |
| 5,250,263 A | 10/1993 | Manz et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| 5,311,896 A | 5/1994 | Kaartinen et al. |
| 5,316,727 A | 5/1994 | Suzuki et al. |
| 5,339,486 A | 8/1994 | Persic, Jr. |
| 5,372,946 A | 12/1994 | Cusak et al. |
| 5,374,395 A | 12/1994 | Robinson et al. |
| 5,411,708 A | 5/1995 | Moscetta et al. |
| 5,427,946 A | 6/1995 | Kricka et al. |
| 5,486,335 A | 1/1996 | Wilding et al. |
| 5,498,392 A | 3/1996 | Wilding et al. |
| 5,503,803 A | 4/1996 | Brown |
| 5,519,635 A | 5/1996 | Miyake et al. |
| 5,559,432 A | 9/1996 | Logue |
| 5,565,171 A | 10/1996 | Dovichi et al. |
| 5,569,364 A | 10/1996 | Hooper et al. |
| 5,580,523 A | 12/1996 | Bard |
| 5,585,069 A | 12/1996 | Zanzucchi et al. |
| 5,585,089 A | 12/1996 | Queen et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,599,432 A | 2/1997 | Manz et al. |
| 5,599,503 A | 2/1997 | Manz et al. |
| 5,603,351 A | 2/1997 | Cherukuri et al. |
| 5,605,662 A | 2/1997 | Heller et al. |
| 5,628,890 A | 5/1997 | Carter et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,652,149 A | 7/1997 | Mileaf et al. |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce et al. |
| 5,726,026 A | 3/1998 | Wilding et al. |
| 5,726,404 A | 3/1998 | Brody |
| 5,731,212 A | 3/1998 | Gavin et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,690 A | 9/1998 | Chow et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,849,486 A | 12/1998 | Heller et al. |
| 5,849,489 A | 12/1998 | Heller et al. |
| 5,849,598 A | 12/1998 | Wilson et al. |
| 5,852,495 A | 12/1998 | Parce et al. |
| 5,856,174 A | 1/1999 | Lipshutz et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,872,010 A | 2/1999 | Karger et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| 5,948,227 A | 9/1999 | Dubrow et al. |
| 5,955,028 A | 9/1999 | Chow et al. |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,972,187 A | 10/1999 | Parce et al. |
| 5,976,336 A | 11/1999 | Dubrow et al. |
| 5,980,704 A | 11/1999 | Cherukuri et al. |
| 5,980,719 A | 11/1999 | Cherukuri et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,012,902 A | 1/2000 | Parce et al. |
| 6,043,080 A | 3/2000 | Lipshutz et al. |

| | | | |
|---|---|---|---|
| 6,046,056 | A | 4/2000 | Parce et al. |
| 6,048,734 | A | 4/2000 | Burns et al. |
| 6,054,034 | A | 4/2000 | Soane et al. |
| 6,056,860 | A | 5/2000 | Amigo et al. |
| 6,057,149 | A | 5/2000 | Burns et al. |
| 6,102,897 | A | 8/2000 | Lang |
| 6,130,098 | A | 10/2000 | Handique et al. |
| 6,168,948 | B1 | 1/2001 | Anderson et al. |
| 6,197,595 | B1 | 3/2001 | Anderson et al. |
| 6,287,254 | B1 | 9/2001 | Dodds |
| 6,306,273 | B1 | 10/2001 | Wainright et al. |
| 6,326,211 | B1 | 12/2001 | Anderson et al. |
| 6,403,338 | B1 | 6/2002 | Knapp et al. |
| 6,534,295 | B2 | 3/2003 | Tai et al. |
| 6,544,734 | B1 | 4/2003 | Briscoe et al. |
| 6,572,830 | B1 | 6/2003 | Burdon et al. |
| 6,576,459 | B2 | 6/2003 | Miles et al. |
| 6,664,104 | B2 | 12/2003 | Pourahmadi et al. |
| 6,670,153 | B2 | 12/2003 | Stern |
| 6,790,330 | B2 | 9/2004 | Gascoyne et al. |
| 6,893,879 | B2 | 5/2005 | Petersen et al. |
| 6,942,771 | B1 | 9/2005 | Kayyem |
| 6,984,516 | B2 | 1/2006 | Briscoe et al. |
| 7,004,184 | B2 | 2/2006 | Handique et al. |
| 7,192,557 | B2 | 3/2007 | Wu et al. |
| 7,270,786 | B2 | 9/2007 | Parunak et al. |
| 7,323,140 | B2 | 1/2008 | Handique et al. |
| 2002/0054835 | A1 | 5/2002 | Robotti et al. |
| 2003/0087300 | A1 | 5/2003 | Knapp et al. |
| 2003/0127327 | A1 | 7/2003 | Kurnik |
| 2008/0050804 | A1 | 2/2008 | Handique et al. |

FOREIGN PATENT DOCUMENTS

| | | |
|---|---|---|
| WO | WO03/012406 A1 * | 2/2003 |
| WO | WO 03/055605 | 7/2003 |

OTHER PUBLICATIONS

Burns et al., "An Integrated Nanoliter DNA Analysis Device," Science 282: 484-487 (1998).

Handique, K. et al., "Mathematical Modeling of Drop Mixing in a Slit-Type Microchannel", J. Micromech. Microeng., 11:548-554 (2001).

Handique, K. et al., "Nanoliter Liquid Metering in Microchannels Using Hydrophobic Patterns", Anal. Chem., 72:4100-4109 (2000).

Handique et al., "On-Chip Thermopneumatic Pressure for Discrete Drop Pumping," Anal. Chem. 73: 1831-1838 (2000).

Handylab, Inc., International Search Report and the Written Opinion for PCT Application No. PCT/US2004/025181 dated Feb. 21, 2005, 13 pages.

He, B. et al., "Microfabricated Filters for Microfluidic Analytical Systems", Analytical Chemistry, vol. 71, No. 7 (1999), pp. 1464-1468.

Ibrahim, M.S. et al., "Real-Time Microchip PCR for Detecting Single-Base Differences in Viral and Human DNA", Analytical Chemistry, vol. 70, No. 9 (1998), pp. 2013-2017.

Khandurina, J. et al., "Microfabricated Porous Membrane Structure for Sample Concentration and Electrophoretic Analysis", Analytical Chemistry, vol. 71, No. 9 (1999), pp. 1815-1819.

Kopp, M.U. et al., "Chemical Amplification: Continuous-Flow PCR on a Chip", Science, vol. 280 (May 15, 1998), pp. 1046-1048.

Kutter, J.P. et al., "Solid Phase Extraction on Microfluidic Devices", J. Microcolumn Separations, vol. 12, No. 2 (2000), pp. 93-97.

Lagally, E.T. et al., "Single-Molecule DNA Amplification and Analysis in an Integrated Microfluidic Device", Analytical Chemistry, vol. 73, No. 3 (2001), pp. 565-570.

Northrup, M.A. et al., "A Miniature Analytical Instrument for Nucleic Acids Based on Micromachined Silicon Reaction Chambers", Analytical Chemistry, vol. 70, No. 5 (1998), pp. 918-922.

Oleschuk, R. et al., "Trapping of Bead-Based Reagents within Microfluidic Systems: On-Chip Solid-Phase Extraction and Electrochromatography", Analytical Chemistry, vol. 72, No. 3 (2000), pp. 585-590.

Ross, P.L. et al., "Analysis of DNA Fragments from Conventional and Microfabricated PCR Devices Using Delayed Extraction MALDI-TOF Mass Spectrometry", Analytical Chemistry, vol. 70, No. 10 (1998), pp. 2067-2073.

Waters et al., "Microchip Device for Cell Lysis, Multiplex PCR Amplification, and Electrophoretic Sizing", Analytical Chemistry, vol. 70, No. 1, pp. 158-162 (1998).

Weigl, B.H. et al., "Microfluidic Diffusion-Based Separation and Detection", Science, vol. 283 (Jan. 15, 1999), pp. 346-347.

* cited by examiner

PROCESSING PARTICLE-CONTAINING SAMPLES

RELATED APPLICATIONS

The present application claims the benefit of U.S. provisional application Nos. 60/491,269, filed Jul. 31, 2003, 60/551,785, filed Mar. 11, 2004, and 60/553,553, filed Mar. 17, 2004, which applications are incorporated herein by reference in their entireties.

FIELD OF THE INVENTION

The present application relates to microfluidic devices and methods for analyzing biological samples, such as bacteria-containing samples.

BACKGROUND OF THE INVENTION

Microfluidic devices include devices with features having dimensions on the order of nanometers to 100 s of microns that cooperate to perform various desired functions. In particular, microfluidic devices perform material analysis and manipulation functions, such as performing chemical or physical analyses.

One type of microfluidic device allows the manipulation of discrete amounts of materials, such as samples and reagents, in addition to or as an alternative to continuous, flowing streams of material. Actuators can move discrete amounts of materials within the microfluidic devices.

SUMMARY OF THE INVENTION

One aspect of the present invention relates to a microfluidic device configured to prepare an enriched particle-containing sample.

In some embodiments, the microfluidic device includes: an input port for receiving a particle-containing liquidic sample, a retention member in communication with the input port and configured to spatially separate particles of the particle-containing liquidic sample from a first portion of the liquid of the particle-containing fluidic sample, and a pressure actuator configured to recombine at least some of the separated particles with a subset of the first portion of the liquid separated from the particles.

In some embodiments, a microfluidic device includes an enrichment region, including: a retention member configured so that liquid of a particle-containing liquid sample received therein exits the enrichment region along an exit path including a first surface of the retention member and particles of the particle-containing liquid sample are retained by the retention member; and a pressure actuator configured to introduce fluid into the enrichment region along an entry path including the first surface of the retention member.

In some embodiments, a device for concentrating particles of a particle-containing fluid includes: a substantially planar substrate including a microfluidic network and a mechanically actuated vacuum generator integral with the substrate, the vacuum generator including an expandable chamber in fluidic communication with the microfluidic network.

In some embodiments, a device for concentrating particles of a particle-containing fluid includes: a first substrate and a second substrate. The first and second substrates define between them at least a portion of a microfluidic network and a chamber. The microfluidic network includes a first end and a second end. The first end is configured to receive a sample including a particle-containing fluid. The second end of the microfluidic network is in fluidic communication with the chamber. The device also includes a manually actuated member operatively associated with the chamber and configured, upon actuation, to increase a volume thereof, so that a pressure within the chamber decreases drawing fluid toward the second end of the microfluidic network.

In some embodiments, a device for concentrating particles of a particle-containing fluid includes a first substrate and a second substrate. The first and second substrates define between themselves at least a portion of a microfluidic network. The microfluidic network includes a filter configured to allow passage of fluid and to obstruct passage of particles that have a minimum dimension greater than a predetermined value with a source of vacuum in fluidic communication with the filter.

In some embodiments, a microfluidic device includes a microfluidic network, including: an input port for receiving a particle-containing fluidic sample (PCFS), a filter configured to retain particles of the PCFS while allowing passage of fluid of the PCFS, and a vacuum generator configurable to be in gaseous communication with the filter. The microfluidic device is configured to: subject a PCFS to a first pressure to expel a first amount of fluid of the PCFS through the filter while retaining particles of the PCFS and subject the retained particles to a second, reduced pressure to withdraw a second, smaller amount of fluid through the filter to prepare an enriched particle-containing fluidic sample.

In some embodiments, a microfluidic device includes a retention member configured to retain particles of the particle-containing fluid while allowing passage of fluid of the particle-containing fluid and a chamber configured to receive fluid that has passed through the retention member. The chamber is configured such that fluid passing therein through the retention member increases a pressure within the chamber.

Another aspect of the invention relates to a method for enriching a particle-containing fluidic sample.

In some embodiments, a method includes inputting a particle-containing liquidic sample into a microliquidic device including a retention member having a first surface, spatially separating a first portion of the liquid of the liquidic sample from particles of the liquidic sample by passing the first portion of the liquid through at least the first surface of the retention member and recombining the retained particles with a subset of the first portion of the liquid.

In some embodiments, a method enriching a sample includes introducing a particle-containing fluidic sample to a microfluidic network, applying a pressure to the fluidic sample to expel a first amount of the fluid of the fluidic sample through a filter configured to retain particles of the fluidic sample within the microfluidic network, and subjecting retained particles of the fluidic sample to a reduced pressure to cause a second, smaller amount of fluid to enter the microfluidic network through the filter and entrain the particles to form an enriched particle-containing sample.

In some embodiments, a method for concentrating particles of a particle-containing fluid, includes introducing a particle-containing fluid to a microfluidic network of a microfluidic device. The microfluidic network includes a filter having a first side. The filter is configured to (a) allow passage of the fluid through the first side and (b) obstruct passage of the particles through the first side. The device also includes a vacuum generator configured to generate a vacuum within at least a portion of the microfluidic network. A first side of the filter is contacted with the particle-containing fluid whereupon at least a first portion of the fluid passes through the filter to the second side of the filter and the particles remain on the first side of the filter. The vacuum generator is actuated to withdraw a subset of the first portion of fluid back through the first side of the filter.

In some embodiments, a method for enriching a particle-containing fluidic sample includes contacting a particle-containing fluidic sample with a filter so that a first portion of the fluid of the PCFS passes through the filter and particles of the PCFS are retained by the filter, the fluid passing through the filter entering a chamber and increasing a pressure therein and allowing a second, smaller portion of the fluid to pass back through the filter and recombine with the particles retained by the filter.

In some embodiments, a method for enriching a particle-containing fluidic sample includes introducing a particle-containing fluidic sample (PCFS) to a sample processing device including a microfluidic network and a chamber separated from the microfluidic network by a retention member, introducing a first amount of the fluid of the PCFS to the chamber by passing the fluid through the retention member. The fluid passing into the chamber increases a pressure therein. Particles of the PCFS are retained by the retention member. A second, smaller amount of fluid is allowed to exit the chamber by passing back through the retention member, the fluid that exits the chamber re-combining with particles retained by the retention member.

In some embodiments, a method for enriching a particle-containing fluidic sample includes driving fluid of the particle-containing fluidic sample through a retention member configured to retain particles of the particle-containing fluidic sample. Fluid passing through the retention member enters a closed chamber and increases a pressure therein. A pathway is provided for fluid present in the chamber to exit therefrom. The pathway includes the retention member such that fluid exiting the chamber passes back through the retention member and recombines with particles retained by the retention member.

In one embodiment of the present invention, a microfluidic device includes one or more thermally actuated elements. A preferred thermally actuated element includes a single source of heat configured to both increase a pressure with a chamber and increase a temperature of a mass of a thermally response substance (TRS) in gaseous communication with the chamber. At the increased temperature, the increased pressure within the chamber is sufficient to move the TRS. For example, the pressure may be sufficient to move the TRS from a side channel of a microfluidic network into a main channel of the network thereby obstructing passage of material in the main channel. Advantageously, use of a single source of heat reduces the amount of power required to actuate such thermally actuated elements. Thermally actuated elements actuated via a single source of heat reduce the complexity of controller electronics and software as compared to thermally actuated elements actuated via two or more sources of heat.

In another embodiment of the present invention, a microfluidic device includes a typically planar substrate including one or more thermally actuated elements. A first side of the substrate includes elements of a microfluidic network, such as a channel and a side channel that intersects the channel. A second, opposed side of the substrate includes a chamber connected to the channel via the side channel. An amount of TRS is disposed in the side channel intermediate the channel and the chamber. Increasing a gas pressure within the chamber may move the TRS into the channel thereby sealing the channel. Advantageously, the chamber and various other elements of the microfluidic network are located on opposite sides of the substrate thereby allowing more efficient use of the space available on the first side of the substrate.

Another aspect of the invention relates to a microfluidic device including a first substrate including first and second opposed surfaces. The second surface defines, at least in part, a chamber. The first surface defines, at least in part, a channel configured to accommodate microfluidic samples and a side channel intersecting the channel and connecting the chamber with the channel. An amount of a thermally responsive substance (TRS) is disposed in the side channel intermediate the chamber and the channel. A second substrate can be mated with the first surface of the first substrate. A third substrate can be mated with the second surface of the first substrate.

Another aspect of the present invention relates to a microfluidic device for processing a cell-containing sample to release intracellular material from cells of the sample.

In some embodiments, a microfluidic device includes a lysing zone, a heat source disposed to heat cell-containing sample present within the lysing zone to release intracellular material from cells of the sample, and first and second valves each having a loading state and a lysing state. When the first and second valves are in the loading state, a cell-containing sample may be introduced to the lysing zone, and, when the first and second valves are in the closed state, the cell-containing sample present in the lysing zone may be heated for a time sufficient to lyse cells of the cell-containing sample without substantial evaporation, e.g., with less than 25% loss, less than 20% loss, or less than 15% loss, of a liquid component of the sample.

The volume of the lysing chamber can be 25 microliters or less, 20 microliters or less, 5 microliters or less e.g. 2 microliters or less.

The valves can include an amount of temperature responsive substance, e.g., wax, to prevent evaporation of the liquid component.

At least one of the valves, e.g., a downstream valve, can be configured as a gate. Prior to loading the sample into the lysing region, the gate is configured in the closed state and includes a mass of temperature responsive substance that obstructs the downstream passage of the material. Upon actuation, at least a portion of the temperature responsive substance passes downstream, thereby opening the gate.

In some embodiments, a microfluidic device for amplifying polynucleotides of a sample includes a reaction zone, a heat source disposed to polynulceotides present within the lysing zone to denature the polynucleotides, and first and second valves each having a loading state and a reaction state. When the first and second valves are in the loading state, a polynucleotide-containing sample may be introduced to the reaction zone, and, when the first and second valves are in the closed state, the polynucleotide-containing sample present in the reaction zone may be heated for a time sufficient to subject the polynucleotides to at least 3 cycles of thermal denaturation and annealing without substantial evaporation of a liquid component of the sample, e.g., without evaporation of more than 10%, e.g., more than 5%, of the liquid component.

One aspect of the invention relates to a microfluidic system including a microfluidic device including a lysing zone. The lysing zone has a volume of less than 25 microliters, e.g., about 20 microliters or less. The lysing zone typically includes an inlet channel and an outlet channel. The microfluidic device also includes one or more valves and/or gates. In a first state, the valves and/or gates are configured to allow a sample to be introduced to the lysing zone. In a second state, the valves and/or gates are closed to limit or prevent liquid or gas from escaping from the lysing zone even when aqueous contents of the lysing zone are heated to, e.g., about 98° for a time of, e.g., about 3 minutes. In a third state, the valves and/or gates are configured to allow sample to exit the lysing zone.

Typically, at least one mass of temperature responsive substance (TRS) is used to inhibit material from exiting the lysing zone in the second state. In some embodiments, in the third state, the TRS may pass downstream along the same channel as material exiting the lysing zone.

BRIEF DESCRIPTION OF THE DRAWINGS

FIG. 6b is a side view of the microfluidic device of FIG. 6a;

DETAILED DESCRIPTION OF THE INVENTION

The present invention relates to microfluidic systems and devices and methods for manipulating and processing materials, such as samples and reagents. Microfluidic devices generally include a substrate that defines one or more microfluidic networks, each including one or more channels, process modules, and actuators. Samples and reagents are manipulated within the micro fluidic network(s). The modules and actuators of the networks are typically thermally actuated. For example, a process module can include a reaction chamber that is heated by a heat source. An actuator may include a chamber that is heated to generate a pressure or a vacuum to move material within the netowork.

Typical samples include particle-containing fluidic samples. The fluid component of the particle-containing fluidic sample may include a gas and/or, a liquid, e.g., a buffer, water, organic solvents, saliva, urine, serum, blood, or combination thereof. In any case, the fluid typically entrains the particles such that the particles tend to move with the fluid.

The particles of the particle-containing fluidic sample generally include cells, such as bacterial cells or cells of an animal, such as a human. The particles may include intracellular material released from such cells. For example, the microfluidic systems may detect (upon optional amplification) polynucleotides, e.g., DNA, released from cells. In some embodiments, the microfluidic system processes DNA released from bacteria cells to determine the presence, absence, and/or abundance of the bacteria, e.g., bacteria associated with Group B streptococcal (GBS) disease. Other particles that may be analyzed include tissue, viruses, spores, fungi, and other microorganisms and material released from within such particles.

Microfluidic Systems and Devices

Figure 1:
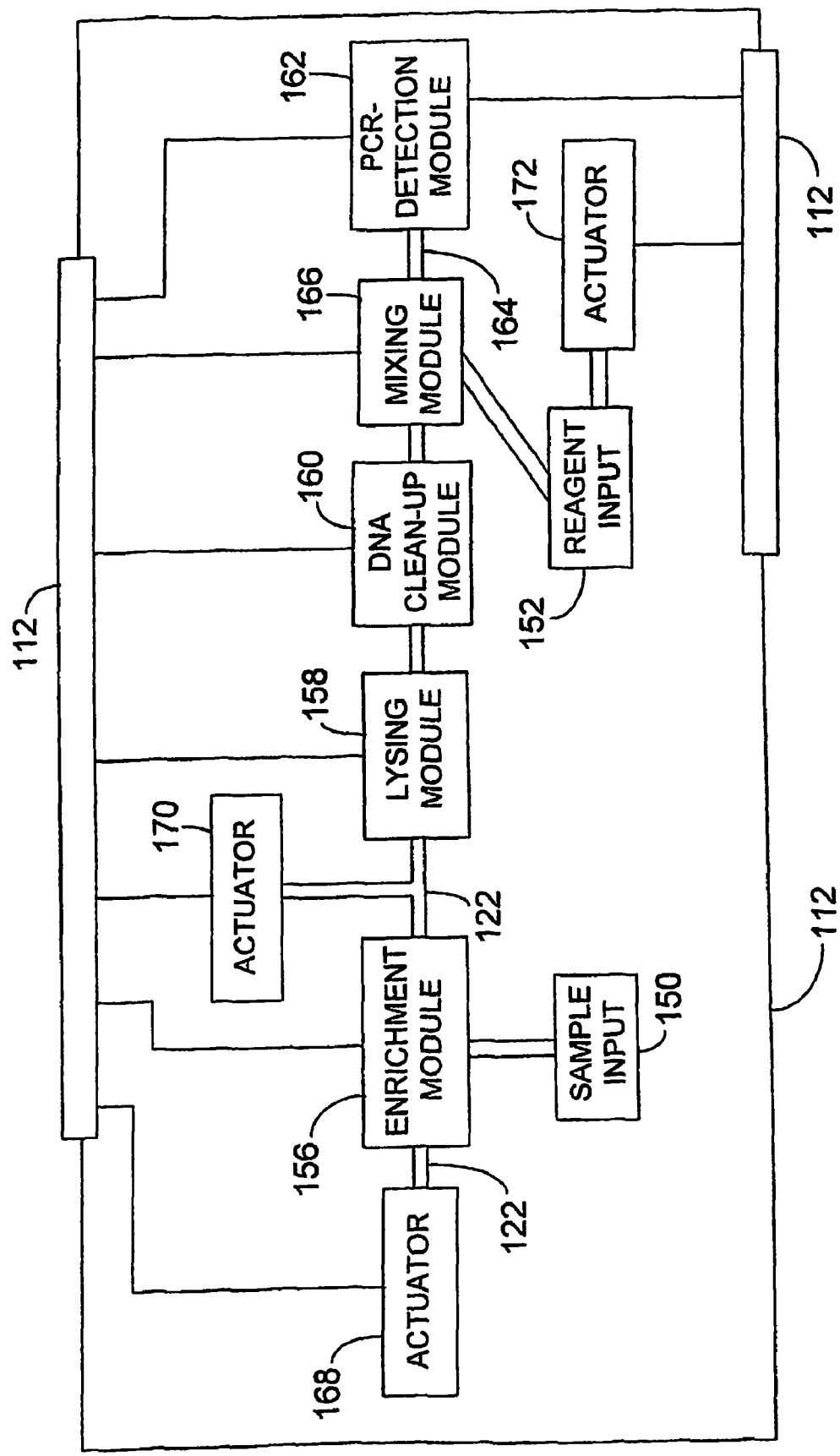
FIG. 1 is a schematic of an exemplary microfluidic device.

Referring to FIG. 1, an exemplary microfluidic network 110 of a microfluidic device has a sample input module 150 and reagent input module 152 to allow sample and reagent materials, respectively, to be input to network 110. Generally, one or both of input modules 150, 152 are configured to allow automatic material input using a computer controlled laboratory robot. Network 110 may also include output ports configured to allow withdrawal or output of processed sample from or by microfluidic network 110.

Within a microfluidic network, material generally travels from upstream locations to downstream locations. For example, sample material generally travels downstream from an input port to other locations within the microfluidic network. In some cases, however, the direction of flow may be reversed.

Locations of network 110 downstream from the input module typically include process modules 156, 158, 160, 166 and 162 for processing the sample and reagent materials. Within these process modules, a sample is subjected to various physical and chemical process steps. For example, enrichment module 156 receives a particle-containing fluid and prepares a fluid sample having a relatively higher concentration of particles. Lysing module 158 releases material from particles of an enriched sample, e.g., the module releases intracellular material from cells. Lysing can be accomplished using, for example, thermal, ultrasonic, mechanical, or electrical techniques. Exemplary lysing modules are discussed in U.S. provisional application No. 60/491,269, filed Jul. 31, 2003, and U.S. patent application Ser. No. 10/014,519, filed Dec. 14, 2001, which applications are incorporated herein by reference.

DNA clean-up module 160 readies polynucleotides, e.g., DNA, released from the particles for detection. For example, DNA clean-up module 160 can be configured to prepare a DNA sample for amplification by polymerase chain reaction. Sample DNA processed by clean-up module 160 moves downstream within network 110. An exemplary DNA clean-up module is discussed in U.S. provisional application No. 60/567,174, filed May 3, 2004, which application is incorporated herein by reference.

Mixing module 166 mixes DNA received from module 160 with reagents from reagent input module 152. Typical reagents include PCR primers, reagents, and controls. Exemplary reagents are used in the amplification and detection of GBS bacteria, such as reagents disclosed in U.S. patent application Ser. No. 10/102,513, filed Mar. 20, 2002, which application is incorporated herein. Reagent materials may be loaded during use and/or stored within the microfluidic device during manufacturing. Certain reagent materials can be lyophilized to extend their storage life. Liquid reagents can be stored within a chamber, e.g., a metalized pouch, for mixing with dried reagents. In some embodiments, a microdroplet having a selected volume is prepared from fluid released from the chamber within the microfluidic device. The microdroplet is combined with dried reagents to prepare a known concentration of reagent materials.

PCR-Detection Module 162 receives DNA released from sample particles and reagents and detects minute quantities of DNA therein. In general, process module 162 is configured to amplify the DNA such as by PCR. Detection is typically spectroscopic, as by fluorescence. In some embodiments, the presence and/or abundance of DNA is detected electrochemically.

PCR-Detection module 162 typically includes more than one amplification/detection chamber. One chamber generally receives and detects (with optional amplification) DNA released from sample particles. Another chamber typically receives and detects (with optional amplification) control DNA, which may be used to indicate whether network 110 is functioning properly. Other modules of network 110, e.g., reagent and mixing modules 152, 166 are configured to accommodate the presence of more than one amplification/detection chamber.

Various modules of microfluidic network 110 are connected, such as by channels 164, to allow materials to be moved from one location to another within the network 110. Actuators 168, 170, 172 associated with the microfluidic device provide a motive force, such as an increased gas pressure and/or a decreased gas pressure to move the sample and reagent material along the channels and between modules. Some gas actuators move materials by reducing a pressure in a downstream portion of a microfluidic network relative to a pressure in an upstream portion of the microfluidic network. The resulting pressure differential moves the material downstream toward the region of reduced pressure. As used herein, the term vacuum does not require the total absence of gas or other material. Rather, a vacuum means a region having at least a reduced gas pressure as compared to another region of the microfluidic device, e.g., a partial vacuum. The volume of channels and chambers associated with a vacuum actuator is typically reduced by placing fluid control elements, e.g., valves or gates, as near to the vacuum chamber of the actuator as is feasible.

First actuator 168 of network 110 moves material downstream from enrichment module 156 to lysing module 158. Upon completion of processing within lysing module 158, a second actuator 170 moves material downstream to DNA clean-up module 160. Subsequently, actuator 170 or an additional actuator moves cleaned-up DNA to mixing module 166, where the material mixes with a reagent moved by actuator 172. Finally, actuator 172, or another actuator, moves the mixed material to PCR-detection module 162.

Because, in some embodiments, each actuator is responsible for moving materials within only a subset of the modules of network 110, sample materials can be controlled more precisely than if a single actuator were responsible for moving material throughout the entire device. The various functional elements, of microfluidic network 110, including the actuators, are typically under computer control to allow automatic sample processing and analysis.

As used herein, the term microfluidic system includes not only a microfluidic device defining a microfluidic network but also the heat sources to operate thermally actuated modules and actuators of the microfluidic device. The heat sources can be integrated with the microfluidic device or incorporated in another component of the microfluidic system such as a receptacle that receives the microfluidic device during operation. The various functional elements, of microfluidic network 110, including the heat sources, are typically under computer control to allow automatic sample processing and analysis. Systems and methods for computer control of microfluidic systems are disclosed in U.S. patent application Ser. No. 09/819,105, filed Mar. 28, 2001, which application is incorporated herein by reference.

Actuators, enrichments modules, lysing modules, and other aspects of microfluidic devices and systems are discussed below.

Microfluidic Devices Including a Vacuum Actuator

As discussed above, actuators can manipulate samples within microfluidic devices by reducing a downstream pressure relative to an upstream pressure within the device. In some embodiments, such actuators are used in combination with an enrichment module to prepare a sample having an enriched amount of particles. The enriched sample can be delivered to a lysing chamber within the microfluidic device. Such devices are discussed below.

Figure 2:
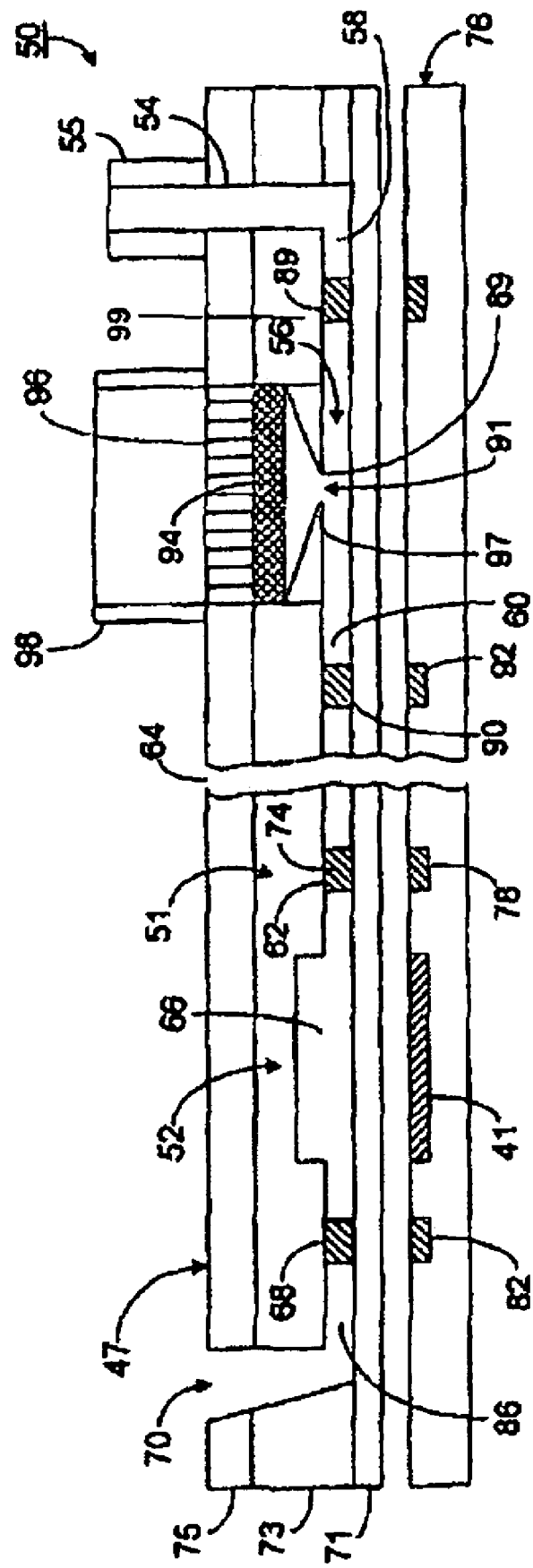
FIG. 2 is a side view of a first embodiment of a microfluidic device.
Figure 3:
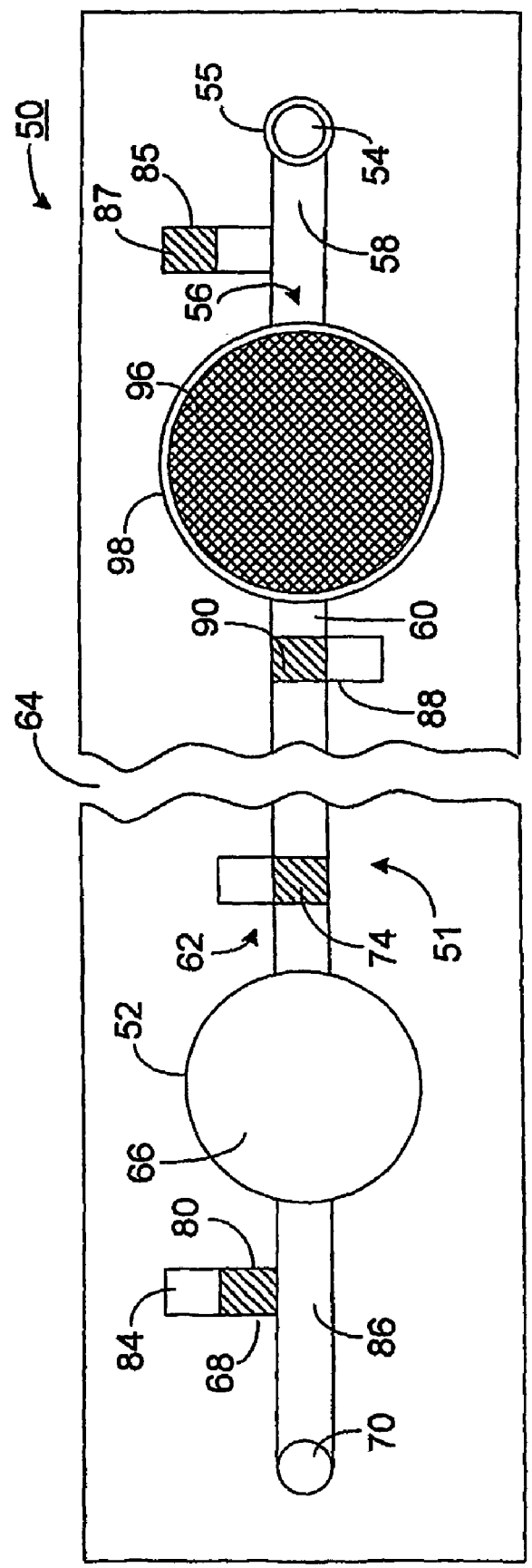
FIG. 3 is a top view of the microfluidic device of FIG. 2.

Referring to FIGS. 2 and 3, a microfluidic device 50 includes a substrate 47 including a first layer 71, a second layer 73, and a third layer 75. The layers of substrate 47 define a microfluidic network 51. Network 51 includes channels, modules, and actuators such as, e.g., those of microfluidic network 110 discussed above. At least some components of network 51 are typically thermally actuated. Thus, substrate 47 may mate in use with a second substrate 76, which includes heat sources configured to be in thermal communication with thermally actuated components of microfluidic network 51. Alternatively, the heat sources may be integral with substrate 47, e.g., substrates 47 and 76 may be integral. Suitable heat sources for actuating thermally actuated components are discussed in copending U.S. application Ser. No. 09/783,225, filed Feb. 14, 2001 and 60/491,539, filed Aug. 1, 2003, which applications are incorporated herein.

In the embodiment shown, network 51 includes an input port 54 by which sample material may be introduced to network 51, an enrichment region 56 connected to input port 54 by a channel 58, and a vacuum generator 52 configured to manipulate material within the microfluidic network and connected to enrichment region 56 by a channel 60. Port 54 may include a fitting 55 to mate with a syringe or other input device and may also include a septum through which a needle or other cannulated sample introduction member may be inserted.

As indicated by a symbolic break 64, microfluidic network 51 may include other modules or components, e.g., a reaction chamber, a lysing module for releasing material from cells or other biological particles, a DNA clean-up module, a reagent mixing chamber, output port, and the like. These other modules or components are typically disposed downstream of enrichment region 56. For example, a typical embodiment includes a lysing chamber to receive an enriched particle sample from enrichment region 56 and an amplification-detection chamber for amplifying and detecting DNA released from particles of the sample.

Vacuum generator 52 includes a gate 62, a chamber 66, a valve 68, and a port 70, which may be in gaseous communication with the ambient environment around device 50. Gate 62 is configured in a normally closed state in which gate 62 obstructs passage of material, e.g., sample material and gas, between chamber 66 and upstream portions of microfluidic network 51 such as enrichment region 56. In an open state, gate 62 allows such passage of material.

Valve 68 is configured in a normally open state in which valve 68 allows passage of material, e.g., gas, along a channel 86 between chamber 66 and port 70. In a closed state, valve 68 obstructs passage of material between chamber 66 and port 70. Valve 68 typically includes a chamber 84 and a mass of thermally responsive substance (TRS) 80. In the closed state, the TRS obstructs passage of material whereas in the open state, the TRS is dispersed or withdrawn from the channel to allow passage of material therealong.

Whether for a gate or a valve, the obstructing mass of TRS can have a volume of 250 nl or less, 125 nl or less, 75 nl or less, 50 nl or less, 25 nl or less, 10 nl or less, 2.5 nl or less, 1 nl or less, e.g., 750 picoliters or less. In some embodiments of a gate or valve, some or all of the TRS passes downstream upon opening the gate or valve. For example, the TRS may pass downstream along the same channel as sample previously obstructed by the TRS. In some embodiments, the TRS melts and coats walls of the channel downstream from the position occupied by the TRS in the closed state. The walls may be at least partially coated for several mm downstream. In some embodiments, the TRS disperses and passes downstream as particles too small to obstruct the channel. Exemplary gates and valves including a mass of TRS are disclosed in U.S. Pat. No. 6,575,188, issued Jun. 10, 2003, which patent is incorporated herein by reference.

Exemplary TRS resist movement at a first temperature and can more readily be moved at a second, higher temperature. The first temperature may be about 25° C. or less and the second higher temperature may be at least about 40° C. The second higher temperature may be a melting temperature or a glass transition temperature of the TRS. Suitable materials include wax, a polymer, or other material having a melting point (or glass transition temperature) of at least 50° C., e.g., of at least 75° C. Preferred TRS materials have melting points (or glass transition temperatures) of less than 200° C., e.g., less than 150° C. Typical TRS materials are hydrophobic but may be hydrophilic.

Raising a temperature within chamber 84 increases a pressure therein. When the temperature within chamber 84 is raised and the temperature of TRS 80 is also raised, the pressure within chamber 84 moves TRS 80 into channel 86 connecting port 70 and chamber 66 thereby obstructing the passage of material, e.g., gas, along channel 86. Substrate 76 includes a heater 82 configured to be in thermal contact with both chamber 84 and TRS 80 when substrates 76 and substrate layer 71 are mated. Actuating heater 82 raises both the temperature within chamber 84 and the temperature of TRS 80 to the second temperature.

Gate 62 is typically a thermally actuated gate including a mass of TRS 74. When substrate layer 71 and substrate 76 are mated, heater 78 and gate 62 are disposed in thermal contact. Actuating heater 78 raises the temperature of TRS 74 to the second temperature.

Even when a pressure differential exists between chamber 66 and upstream portions of network 51, the TRS 74, when at the first temperature, prevents the passage of material between chamber 66 and upstream portions of network 51. When the temperature of TRS 74 is raised to the second temperature, such a pressure differential is typically sufficient to move and/or disperse TRS 74 allowing material, e.g., gas, to pass into chamber 66 from upstream portions of network 51.

When both gate 62 and valve 68 are in the closed state, chamber 66 is configured to maintain a pressure that is less than about 90%, less than about 80%, less than about 70%, less than about 60%, less than about 50%, or less than about 35% of the pressure acting upon the opposite side of valve 68. The pressure acting upon the opposite side of valve 68 is typically the ambient pressure around device 50, e.g., about 1 atmosphere. Generally, the reduced pressure within chamber 66 can be maintained for at least 15 seconds, at least 30 seconds, at least 60 seconds, at least 120 seconds, e.g., at least 300 seconds.

Valves and gates in accord with the present invention may have identical structures with the exception that, unless otherwise specified, a valve is normally configured in an open state and a gate is normally configured in a closed state.

A method for preparing a vacuum within chamber 66 typically includes the at least partial evacuation of gas from chamber 66 and the sealing of the evacuated chamber to prevent material from re-entering the chamber. Evacuation is generally achieved by heating chamber 66. For example, when substrate layer 71 and substrate 76 are mated, chamber 66 is in thermal contact with a heat source 41 of substrate 76. Actuation of the heat source 41 raises the temperature of material present within chamber 66. The material within the chamber may include, e.g., a gas and/or vaporizable material such as a liquid or a material that is capable of sublimation at a temperature of between about 50° C. and about 200° C.

Vacuum generator 52 is typically used to manipulate materials within network 51 of device 50. In some embodiments, vacuum generator cooperates with enrichment region 56 to prepare an enriched sample. The enrichment region is now discussed in greater detail.

Enrichment region 56 includes a retention member 94, a valve 85, and a downstream gate 88. Retention member 94 generally includes a filter to selectively retain particles of a particle-containing sample as compared to fluid (e.g. a liquid) of the particle-containing sample, such as to allow the passage of fluid but limit or prevent the passage of the particles. Typically, retention member 94 allows the passage of fluid therethrough but retains particles by size exclusion. For example, retention member 94 allows fluid to exit enrichment region 56 by passing through retention member 94 but retains particles within the enrichment region. Fluid that passes through retention member 94 enters a reservoir 98 configured to contain such fluid.

In some embodiments, retention members are configured to retain, such as by size exclusion, bacteria, e.g., GBS from culture and clinical samples. An exemplary retention member is a polycarbonate track-etch filter defining, e.g., 0.6 μm pores, such as is available from Poretics.

Enrichment region 56 may communicate with retention member 94 via a hole 89, which may open to a cavity 91 defined at least in part by a surface 97 of retention member 94. Cavity 91 allows the particle-containing sample to contact retention member 94 over a surface area that is greater than a surface area of hole 89. Cavity 91 may be tapered as shown to facilitate entry of fluid and particles to and removal of fluid and particles from cavity 91. As an alternative to cavity 91, hole 89 may communicate with a network of channels that distribute fluid over a surface 97 of retention member 94.

Reservoir 98 may be sealed, such as by a fluid impermeable membrane (not shown), to prevent fluid expelled through retention member 94 from leaking into the surrounding environment. The sealed volume of the reservoir may be as great as or greater than the total internal volume of enrichment chamber 56 and portions of network 51 downstream thereof.

A retention member support 96 helps retain retention member 94 in position against internal pressure created by the introduction of sample and the passage of fluid through retention member 94. Support 96 may be a grid fabricated as part of substrate layer 73.

Gate 88 has a normally closed state to obstruct passage of material between enrichment region 56 and downstream portions of microfluidic network 51. Gate 88 has an open state in which material may pass from enrichment region 56 to downstream portions of network 51. Gate 88 may be a thermally actuated gate including a mass of TRS 90 and actuated by a heat source 92 of substrate 76.

Valve 85 has a normally open state in which material may pass between upstream portions of microfluidic network 51 and enrichment region 56. Valve 85 has a closed state, which obstructs material from passing between enrichment region 56 and upstream regions of microfluidic network 51. Valve 85 may be a thermally actuated valve including a mass of TRS 85 and a chamber 87. Substrate 76 includes a heat source 93 configured to actuate valve 85 as discussed for valve 68.

Enrichment region 56 of device 50 may be operated as follows. A particle containing fluid sample is introduced to network 51, e.g., via port 54, such as by using a syringe or other sample introduction device. The amount of sample introduced may be at least, e.g., 250 microliters, at least 500 microliters, or at least 1,000 microliters. The amount of fluid, e.g., liquid, introduced may be, e.g., less than 10,000 microliters, less than 5,000 microliters, or less than 2,500 microliters. Enrichment region 56 is typically configured so that (with downstream gate 88 closed) fluid entering device 50 must pass through retention member 94 to exit the enrichment region. The particle-containing fluidic sample passes along channel 58 into enrichment region 56.

Retention member 94 spatially separates at least some and preferably most of the fluid of the received fluidic sample from particles of the received fluidic sample. For example, liquid of a fluidic sample may pass through or beyond at least surface 97 of retention member 94 whereas retention member 94 retains particles of the fluidic sample, such as at surface 97 thereof. Fluid, e.g., liquid, that passes through or beyond surface 97 exits enrichment region 56 and may pass into reservoir 98. Fluid that has passed beyond surface 97 may be described as having been expelled from the microfluidic network.

Retention member 94 retains particles of the fluid sample, such as by size exclusion and/or by adsorption and/or absorption of the particles. Thus, once the fluidic sample has been introduced, reservoir 98 contains fluid of the sample whereas particles of the sample are retained within enrichment region 56, such as at surface 97 of retention member 94. However, some of the fluid of the fluidic sample may remain within the enrichment region 56 (interior to surface 97) and in contact with the retained particles. This amount of fluid is typically less than about 50%, less than about 25%, less than about 10%, less than about 5%, e.g., less than about 2% relative to the total amount of fluid received by enrichment region 56. The total amount of fluid received by the enrichment region 56 is typically between about 1 and 10 ml.

Once a sufficient amount of sample has been introduced, valve 85 is actuated to the closed state thereby preventing passage of material between enrichment region 56 and upstream portions of network 51, e.g., port 54. Particles retained by the filter may be moved away from the filter by causing fluid to pass into enrichment region through retention member 94 along a path that is substantially opposite to the path followed by fluid of the fluidic sample in passing beyond surface 97 and into reservoir 98.

In some embodiments, device 50 is configured such that a gas pressure downstream of enrichment region 56, e.g., downstream of gate 88, is less than a gas pressure external to surface 97 of retention member 94. When gate 88 is opened, the pressure differential causes some fluid, e.g., fluid within reservoir 98, e.g., liquid of the particle-containing sample, to enter enrichment region 56, combine with retained particles therein and move the particles away from the retention member 94. A vacuum may be used to obtain the pressure differential.

A vacuum may be prepared as follows. With valve 68 (of vacuum generator 52) configured in the open state and at least one gate intermediate vacuum generator gate 52 and enrichment region 56 (e.g., gate 62) configured in the closed state, heat source 41 is actuated thereby raising a temperature of material within chamber 66. Gas present within the chamber expands and at least some of the expanded gas exits network 51 via port 70. If a liquid is present within chamber 66, the liquid may vaporize with at least some of the vapor also exiting via port 70. Similarly, the elevated temperature may sublimate a solid present within chamber 66. Once the temperature within chamber 66 has been raised to a given temperature for a given time, valve 68 is closed and the temperature within chamber 66 is allowed to decrease.

Upon the reduction of temperature within chamber 66, the pressure, e.g. the total gas and vapor pressure therein, decreases and creates a pressure differential between chamber 66 and enrichment region 56. Once the pressure differential has reached a sufficient level, chamber 66 and enrichment region 56 are brought into gaseous communication such as by actuating any closed gates (e.g., gate 62 and/or 90) along channel 60. With chamber 66 and enrichment region 56 in communication, a pressure differential is created between a pressure of gas above fluid in reservoir 98 and a pressure within enrichment region 56. The pressure differential draws a portion of the fluid present in reservoir 98 through retention member 94 and into enrichment region 56. The fluid preferably passes through retention member 94 in an opposite direction from the direction taken by fluid during expulsion through retention member 94. The direction of flow may be substantially orthogonal to layer 73. The direction of flow may be substantially orthogonal to a plane defined by network 51.

The fluid entering enrichment region 56 combines with particles retained by retention member 94 during sample introduction and forms an enriched particle-containing sample typically including a smaller volume fluid, e.g., liquid, than was introduced into network 51 and a substantial portion of the particles that were retained by retention member 94. The amount of fluid that passes into, e.g., back into, enrichment region 56 through retention member 94 is typically less than 50%, less than 10%, less than 2.5%, or less than 1% of the volume of fluid, e.g., liquid, introduced with the sample. For example the amount of fluid, e.g., liquid, that passes into enrichment region 56 through retention member 94 may be less than 50 microliters, less than 25 microliters, less than 15 microliters, less than 10 microliters, or less than 5 microliters. The retention member 94 no longer retains the particles of the enriched particle-containing sample so that the enriched particle-containing sample moves away from the retention member.

It should be understood that at least a portion of the fluid expelled through retention member 94 and into reservoir 98 may be replaced with other fluid, such as fresh buffer or a different buffer. In this case, the fluid passing into enrichment region 56 through retention member 94 includes at least some and perhaps substantially all of the other fluid. Thus, the fluid entering into the enrichment region 56 through retention member 94 is not limited to the fluid that was expelled upon introducing the particle-containing sample.

In addition to preparing the enriched fluid, the pressure differential is typically sufficient to also move the enriched fluid into a downstream portion of microfluidic network 51.

However, the downstream movement can be accomplished using another vacuum generator or a source of positive pressure source in addition to or as an alternative to vacuum generator 52.

Typically enrichment ratios, i.e., the volume concentration of particles in the enriched fluid relative to the volume concentration of particles in the introduced fluid, are at least 5, at least 10, at least 25, at least 50 or at least 100. The enriched fluidic sample may be withdrawn from network 51 or subjected to further processing and or analysis therein.

Figure 4:
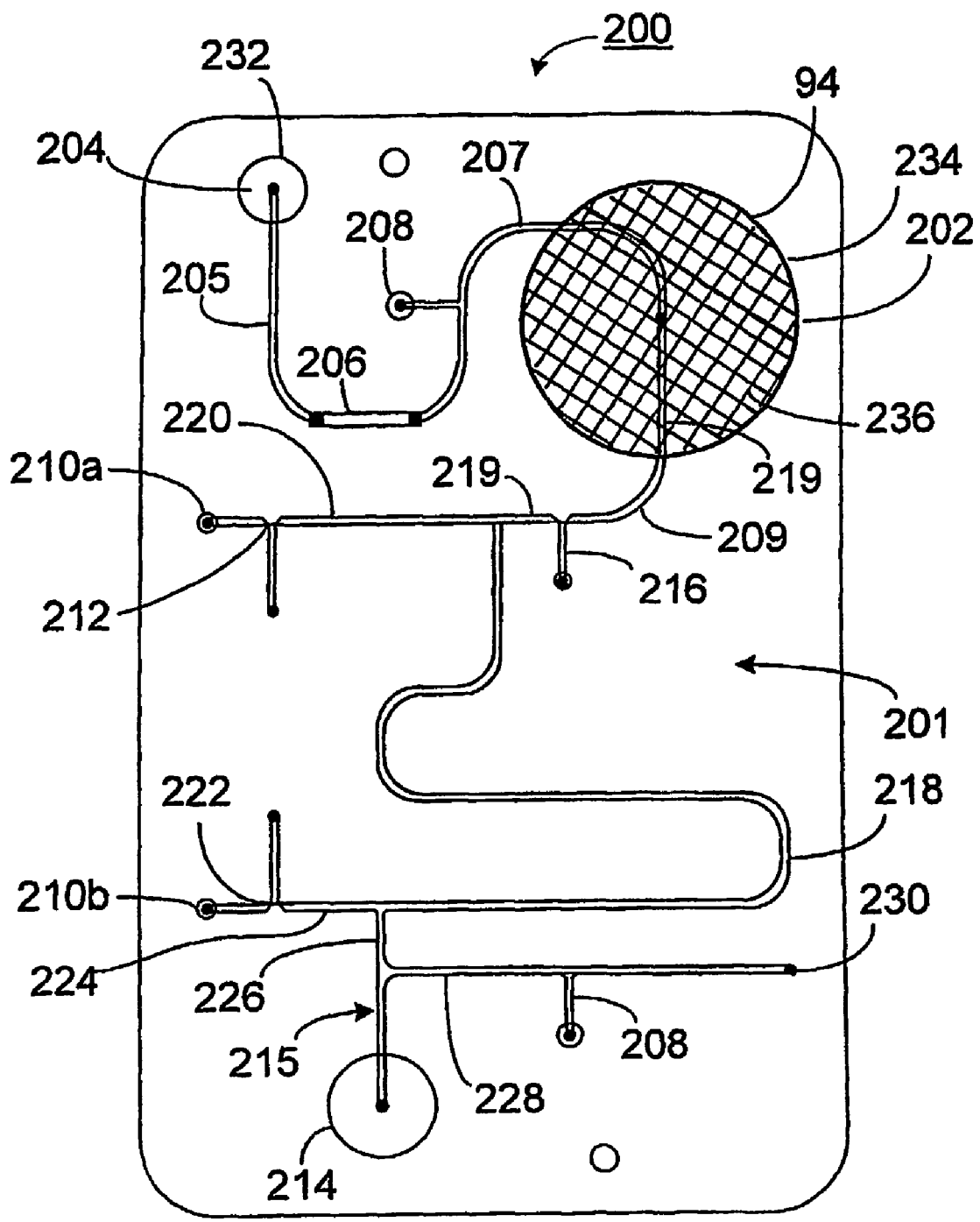
FIG. 4 is a top view of a second embodiment of a microfluidic device.
Figure 5:
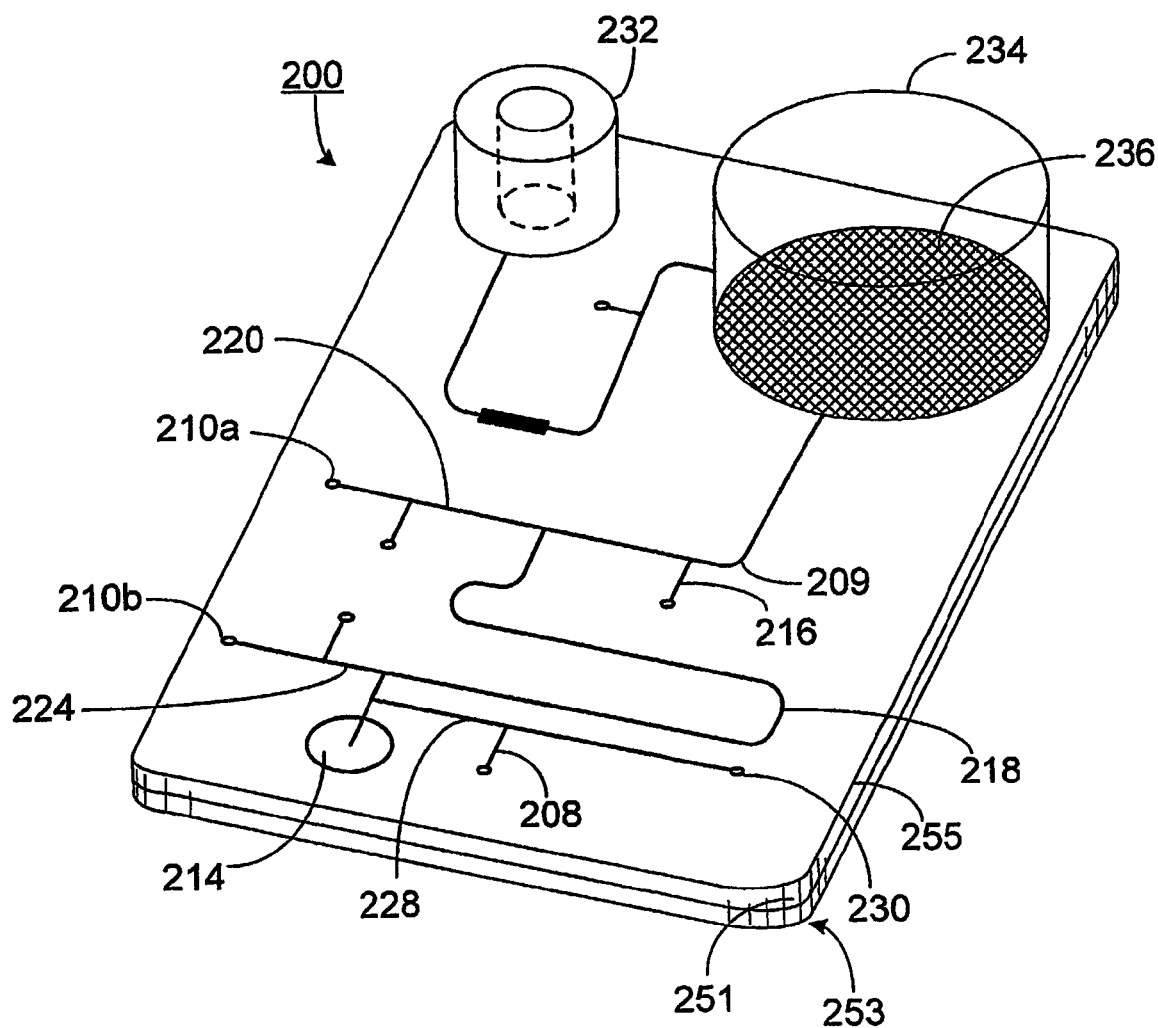
FIG. 5 is a top perspective view of the microfluidic device of FIG. 4.

Referring to FIGS. 4 and 5, a microfluidic device 200 receives a sample, e.g., a particle-containing sample, and enriches the sample to prepare an enriched sample including a greater relative concentration of the particles. In the embodiment shown, device 200 includes a microfluidic network 201 including an input port 204, a channel 205 along which sample material received via input port 204 may pass, a vent 206 configured to allow gas accompanying the received sample material to exit network 201, and a channel 207 disposed downstream of vent 206. An enrichment region 202 is located downstream of channel 207.

Input port 204 can include a fitting 232 (FIG. 5) configured to mate with a syringe or other input device. Vent 206 may include a gas permeable hydrophobic membrane, e.g., a porous polytetrafluoroethylene membrane available from W. L. Gore, Inc.

Channels 205 and 207 are separated by a valve 208, which generally has a normally open state configured to allow at least downstream passage of material from channel 205 to channel 207. Valve 208 can be actuated to a closed state configured to obstruct passage of material between enrichment region 202 and portions of network 201 upstream of valve 208. Valves of device 200 may be configured as thermally actuated valves discussed for device 50.

Enrichment region 202, which may be configured as enrichment region 56, receives sample material introduced via port 204 and prepares an enriched sample enriched in a desired particle. Enrichment region 202 includes a retention member 94, a retention member support which may be configured as support 96, and a reservoir 234, which may be configured as reservoir 98.

Network 201 also includes a channel 209 located downstream of enrichment region 202 to receive enriched sample material therefrom. Channel 209 includes a gate 216 configured to selectively permit the downstream passage of material between enrichment region 202 and portions of network 201 downstream of gate 216.

Gate 216 has a normally closed state which obstructs the passage of material, e.g., enriched sample and/or gas, between enrichment region 202 and portions of network 201 downstream of gate 216. Gate 216 may be actuated to an open state in which material may pass between enrichment region 202 and downstream portions of network 201. Gates of device 200 may be configured as thermally actuated gates discussed for device 50.

Gate 216 is connected to downstream portions of network 201 via a channel 219. In the embodiment shown, network 201 includes an output port 210a connected to channel 219 via a channel 220. Enriched sample material may be withdrawn manually or output automatically from port 210a by device 200. A gate 212 having a normally closed state selectively obstructs or permits passage of material between channel 220 and output port 210a.

Other downstream portions of network 201 are connected to channel 219 via a channel 218. For example, an output port 210b is connected to channel 218 via a channel 224. Enriched sample material may be withdrawn manually or output automatically from port 210b by device 200. A gate 222 having a normally closed state selectively obstructs or permits passage of material between channel 218 and output port 210b.

Device 200 can be configured to enrich a sample as follows. Gate 216 is configured in the closed state obstructing passage of material between enrichment region 202 and downstream portions of network 201. Valve 208 is configured in the open state. An amount of sample material is introduced to channel 205, such as by using a syringe configured to mate with fitting 232. The amount of sample introduced may be as described for device 50. The introduced sample material passes vent 206, which allows gas to exit channel 205 but resists the exit of fluid and particles of the sample material. Sample material passes downstream of vent 206 and is received by enrichment region 202.

Retention member 94 allows fluid of the sample material to exit enrichment region 202 but retains particles, such as by allowing the passage of fluid but limiting or preventing the passage of the particles as described above. The fluid is expelled through retention member 94 and into reservoir 234, which may be sealed as for reservoir 98. Particles of the sample are retained within enrichment region 202 as described above.

Network 201 may be configured to manipulate, e.g., move, material therein by using pressure differentials therein. For example, the creation of a relatively decreased pressure in a first portion of the network relative to a pressure in a second portion of the network can be used to urge material from the second toward the first portions of the network. The relatively decreased pressure can be created by a decrease in the absolute pressure in the first portion and/or an increase in the absolute pressure in the second portion. In the embodiment shown, device 200 includes a vacuum generator 215 configured to create a decreased pressure at locations downstream of enrichment region 202 relative to a pressure within enrichment region 202 and/or a pressure above fluid within reservoir 234. Device 200 can use the pressure differential to move enriched sample material from enrichment region 202 to downstream portions of network 201.

Vacuum generator 215 includes a chamber 214, a port 230, and a valve 208. Chamber 214 communicates with channel 220 (and therefore channel 209 and enrichment region 202 when gate 216 is in the open state) via a channel 218 and a channel 226. Chamber 214 communicates with port 230 via a channel 228. Valve 208 permits selective obstruction of channel 228 so that the passage of material, e.g., gas, between chamber 214 and port 230 may be obstructed. Port 230 and valve 208 may be configured and operated as port 70 and valve 68 respectively.

Device 200 may be configured for creating a partial downstream vacuum as follows. Gate 209 is configured in the closed state thereby preventing or at least limiting the passage of gas between enrichment region 202 and chamber 214. If either of output ports 210a, 210b are present, gates 212, 222 are configured in the closed state, thereby preventing or at least limiting the passage of gas into or out of network 201 via ports 210a, 210b. Valve 208 is configured in the open state thereby allowing the passage of material, e.g., gas between chamber 214 and port 230, which typically provides the only passage for gas to exit network 201 from chamber 214. Gas present within chamber 214 is heated causing the gas to expand. At least some of the expanded gas exits chamber 214 (and therefore network 201) via port 210. When the gas has been expanded to a desired extent, valve 208 is closed and the remaining gas is allowed to cool causing a partial vacuum to form within chamber 214.

Device 200 may be configured to use a partial vacuum with chamber 214 to prepare an enriched sample as follows. A particle-containing fluid sample is introduced as described above so that retention member 94 retains particles. Fluid is present within reservoir 234. The fluid may include fluid expelled through retention member 94 and/or fresh or additional fluid as described for device 50. The partial vacuum within chamber 214 is prepared. Gate 216 is actuated, such as by heating a TRS thereof, thereby placing chamber 214 in communication with enrichment region 202 and creating a pressure differential between the pressure of a gas above the fluid in reservoir 234 and chamber 214. The pressure differential operates as discussed for enrichment region 56 to withdraw an amount of fluid back through retention member 94 and back into enrichment region 202 to prepare an enriched particle containing sample. The enriched sample may be prepared in the same amounts and with the same properties as for device 50.

In addition to preparing the enriched fluid, the pressure differential between chamber 214 and above fluid in reservoir 234 is typically sufficient to also move the enriched fluid into a downstream portion of microfluidic network 201. However, the downstream movement can be accomplished using another vacuum generator or a source of positive pressure source in addition to or as an alternative to vacuum generator 215. Gate 216 may be re-sealed thereby preventing the passage of additional material between enrichment region 202 and downstream portions of network 201.

Vacuum generator 215 may be actuated a second time to move the enriched sample again. For example, at least one of gates 212, 222 may be actuated to place ports 210a, 210b in communication with network 201. Gas within chamber 214 is heated creating a pressure increase that drives the enriched sample toward ports 210a, 210b. Alternatively, network 201 may contain additional modules, e.g., a lysing module, a reagent mixing module, a reaction module, etc., for subjecting the enriched sample to further processing within network 201. Additional vacuum generators or pressure generators may be added to effect further movement of the enriched and or processed sample within these modules.

Figure 6A:
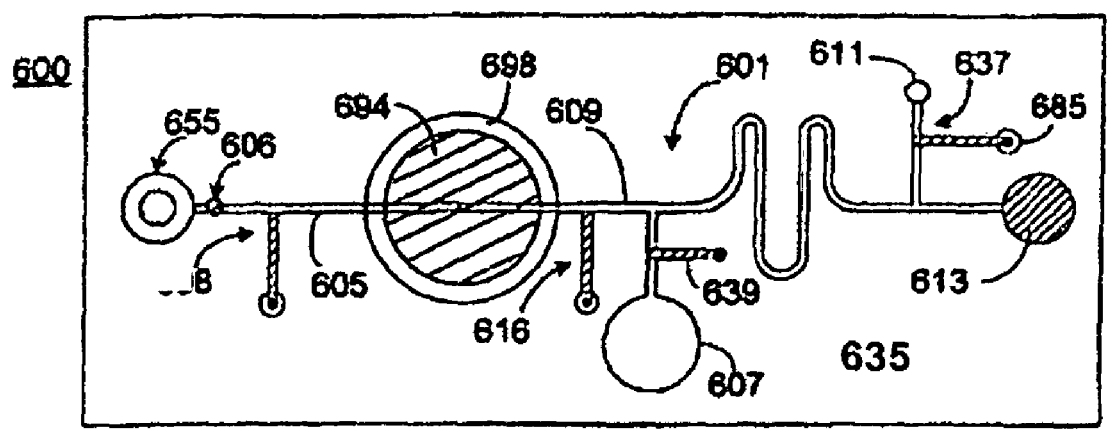
FIG. 6a is a top view of a third embodiment of a microfluidic device.
Figure 6B:
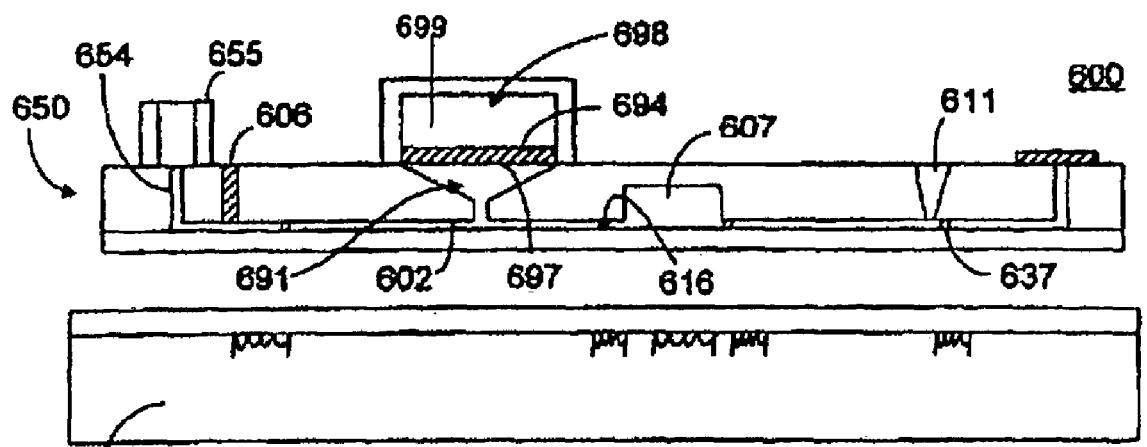

Referring to FIGS. 6a and 6b, a microfluidic device 600 is configured to receive an amount of a particle-containing fluidic sample and to prepare an enriched sample including a greater abundance of the particles. The preparation of the enriched sample includes spatially separating particles of the particle-containing sample from (at least some) fluid of the sample, e.g., liquid of the sample. Device 600 uses pressure created during the spatial separation to recombine a subset of the fluid that was separated from the particles with the particles. These and other aspects of device 600 are discussed below.

Device 600 includes a microfluidic network 601 including an input port 654, a sample enrichment region 602 connected to the sample port by a channel 605, a pressure actuator 607 located downstream of enrichment region 602 and connected thereto by a channel 609, and an output port 611 in communication with channel 609.

Channel 605 includes a vent 606 configured to allow gas to exit channel 605. Vent 606 may have features of vent 206 discussed above.

Channel 605, upstream of enrichment region 602, includes a valve 608 to selectively obstruct passage of material between input port 654 and enrichment region 602. Valve 608 may have features of valve 208 or other valves (or gates) discussed herein. Valve 608 is preferably configured to have a normally open state that allows material to pass along channel 605.

As an alternative or in combination with valve 608, device 600 can include a 1-way valve configured to allow sample to enter channel 605 and pass downstream but configured to limit or prevent material, e.g., gas, from passing upstream from chamber 699 and exiting device 600 via port 654. An exemplary valve is a duckbill valve available from Minivalve International, Oldenzaal, The Netherlands. Such a valve can be located at port 654, e.g., in combination with fitting 655, or disposed along channel 605.

Channel 609, downstream of enrichment region 602, includes a gate 616 to selectively allow passage between enrichment region 602 and downstream locations of microfluidic network 601. Gate 616 may have features of gate 216 or other gates (or valves) discussed herein. Gate 616 is generally configured to have a normally closed state that obstructs passage of material between enrichment region 602 and downstream locations of network 601.

Network 601 includes a passage 635 that connects output port 611 and channel 609. The passage 635 includes a gate 637 to selectively obstruct or allow passage between channel 609 and output port 611. Gate 637 may have features of gate 216 or other gates (or valves) discussed herein. Gate 637 is generally configured to have a normally closed state that obstructs passage of material between channel 609 and output port 611.

Pressure actuator 607 includes a gate 639 to selectively allow passage between actuator 607 and channel 609. Gate 639 may have features of gate 216 or other gates (or valves) discussed herein. Gate 639 is generally configured to have a normally closed state that obstructs passage of material between actuator 607 and channel 609.

Enrichment region 602 includes a retention member 694 to spatially separate particles of a particle-containing sample from fluid of the particle-containing sample. Retention member 694 preferably allows fluid, e.g., gas and/or liquid, to pass therethrough and into reservoir 698. Retention member 694 typically retains particles within a cavity 691 that is at least in part defined by a surface 697 of retention member 694. Enrichment region 602 may have features of enrichment region 56 or other enrichment regions discussed herein. Retention member 694 may have features of retention member 94 or other retention members discussed herein. For example, retention member 694 may operate to allow the passage of fluid but limit or prevent the passage of the particles by size exclusion, binding, and/or adsportion.

Figure 6C:
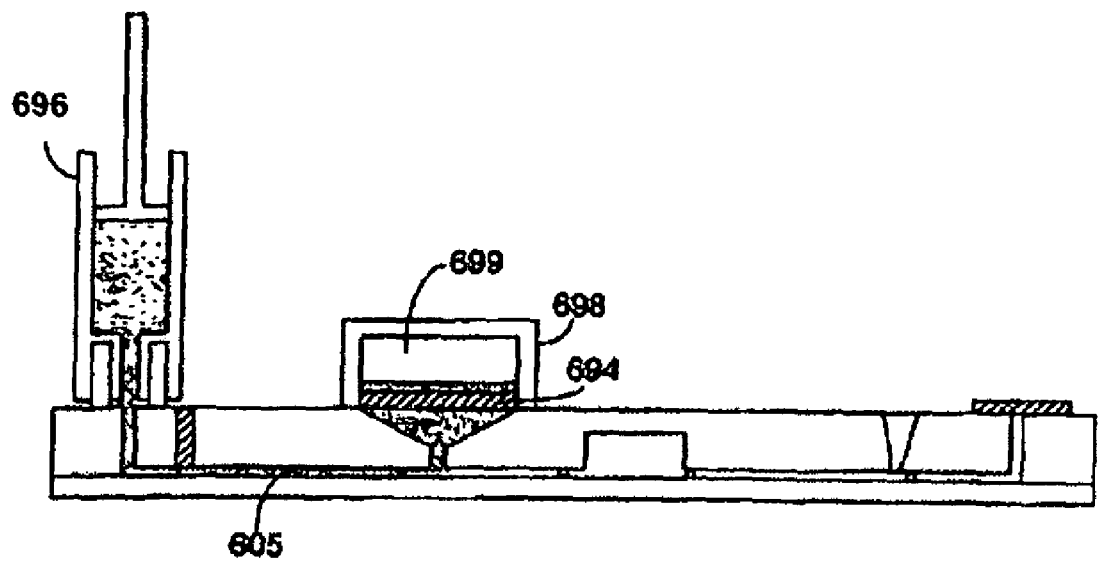
FIGS. 6c and 6d illustrate the introduction of sample material to the microfluidic device of FIG. 6a, more sample material having been introduced in FIG. 6d than in FIG. 6c.
Figure 6D:
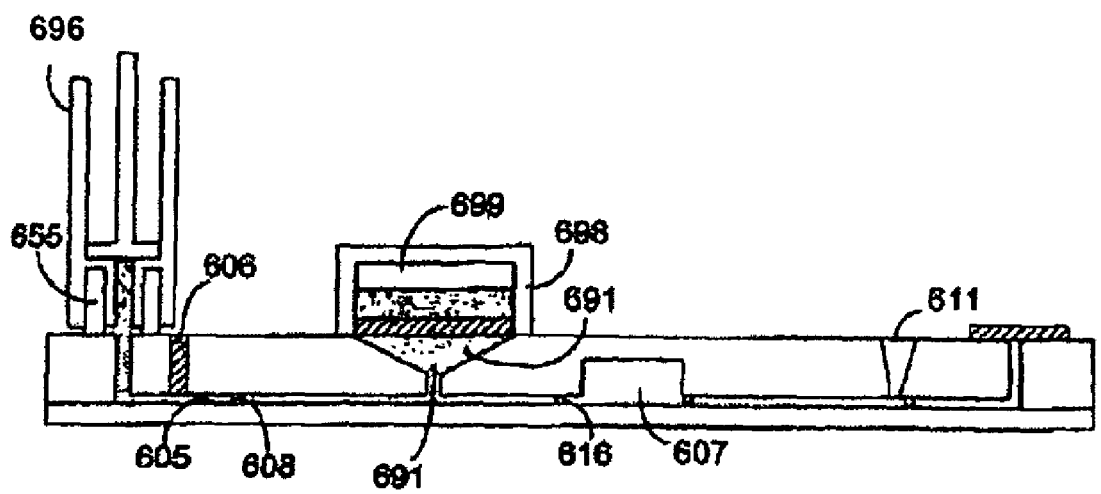

Referring also to FIGS. 6c and 6d, reservoir 698 defines a substantially gas impermeable chamber 699. Fluid that enters chamber 699, such as by passing through retention member 694, decreases a free volume thereof and increases a pressure therein. Thus, the pressure within chamber 699 is greater in FIG. 6d than in 6c because more fluid has been introduced to the chamber 699. The force needed to overcome the introduction of fluid to chamber 699 is provided during the introduction of sample to device 600.

Chamber 699 may include a valve, e.g., a pressure relief valve (not shown), configured so that each introduction of sample into device 600 creates the same pressure within chamber 699. Exemplary pressure relief valves are umbrella valves available from Minivalve International. A pressure relief valve can be used in any pressure chamber of devices herein. Typically, the relief valve opens when the pressure differential between pressure within chamber 699 and pressure external to chamber 699 exceeds about 0.5 psi, about 1 psi, about 2 psi, or about 3 psi. Larger volume chambers typically have valves that open at lower pressures than smaller volume chambers.

Device 600 may be operated as follows. A particle-containing sample is introduced to device 600, such as by using a sample introduction device, e.g., a syringe 696, mated with fitting 655 of input port 654. With valve 608 in the open state and gate 616 in the closed state, sample material passes along channel 605 into enrichment region 602. Pressure created by the sample introduction device drives fluid of the sample through retention member 694 and into chamber 699 of reservoir 698. As discussed above, the entry of fluid into chamber 699 increases the pressure therein. Retention member 694 retains particles of the sample within cavity 691 of enrichment region 602.

Once a sufficient amount of sample material has been introduced, the enrichment region may be sealed to prevent pressure created within chamber 699 from being vented or driving material out of enrichment region 602. For example, valve 608 may be actuated to the closed state to prevent passage of material between input port 654 and enrichment region 602 along channel 605. With both valve 608 and gate 616 in the closed state, device 600 maintains the pressure within chamber 699.

To prepare an enriched particle-containing fluidic sample, gate 616 is actuated to the open state thereby providing a passage for material to exit chamber 699. The relatively greater pressure within the chamber drives fluid therein through retention member 694 and into cavity 691 of enrichment region 602. Thus, the fluid passes through retention member 694 in an opposite direction from the fluid that entered chamber 699 through retention member 694.

Typically, only a subset of fluid that entered chamber 699 passes back through retention member 694. The amount of fluid, e.g., liquid, that passes into enrichment region 602 through retention member 694 is typically less than 50%, less than 10%, less than 2.5%, or less than 1% of the volume of fluid, e.g., liquid, introduced with the sample. For example the amount of fluid, e.g., liquid, that passes into enrichment region 602 through retention member 694 may be less than 50 microliters, less than 25 microliters, less than 15 microliters, less than 10 microliters, or less than 5 microliters. Thus, device 600 prepares an enriched particle-containing sample including particles of the particle-containing sample and a subset of the fluid that was originally introduced to device 600.

A volume of a downstream portion of network 601 may determine the volume of fluid (e.g., the volume of the subset) that recombines with the particles. Typically, the downstream portion is defined between enrichment region 602 and a downstream vent. For example, downstream channel 609 includes a vent 613, e.g., a gas-permeable hydrophobic membrane, that allows gas to exit network 601 but substantially prevents liquid from exiting network 601. With gate 616 open, pressure within chamber 699 drives the enriched sample along channel 605 toward the vent 613. Gate 637 prevents material from exiting network 601 via port 611. Gate 639 prevents material from entering pressure actuator 607.

Upon the enriched sample material reaching vent 613, channel 609 is filled with enriched sample material and the downstream passage of additional material from enrichment region 602 is limited or prevented. Thus, the downstream volume of channel 609 defines the volume of liquid that may exit chamber 699 and recombine with particles to prepare the enriched sample material. Although the downstream passage of additional material is limited or prevented by vent 613, the pressure within chamber 699 may be vented, e.g., by re-opening valve 608. Alternatively, or in combination, gate 616 (or a valve downstream of chamber 699, not shown) may be re-closed (or closed) to isolate chamber 699 from channel 609.

Device 600 may include additional modules, such as one or more of those of system 110 of FIG. 1. Such modules are preferably configured to further process the enriched sample, such as by lysing cells thereof, removing polymerase chain reaction inhibitors, mixing the enriched sample with reagent, and the like. For devices including such modules, passage 635 may connect with these modules rather than leading to output port 611. In such embodiments, device 600 may be configured to drive a known volume of the enriched sample material downstream toward the additional modules. Alternatively, device 600 may be configured to expel a known amount of the enriched sample material from the device via port 611.

A known amount of enriched sample material may be driven downstream or expelled as follows. With enriched sample material present in channel 609, pressure actuator 607 is actuated to generate pressure therein. For example, actuator 607 may include a gas chamber in thermal communication with a heat source. The heat sources may be integral with device 600 or located in a separate substrate 671 as for device 50. In any event, heat from the heat source expands gas present in the chamber of actuator 607 and generates pressure. To move the enriched sample, gates 637 and 639 are opened allowing pressure within the actuator 607 to move the enriched sample. The volume of enriched sample is determined by the volume of network 601 downstream of actuator 607 and upstream of vent 613. Thus, device 600 may be configured to prepare and/or deliver an enriched sample having a known volume. The volume of a prepared and a delivered sample need not be the same.

Figure 7:
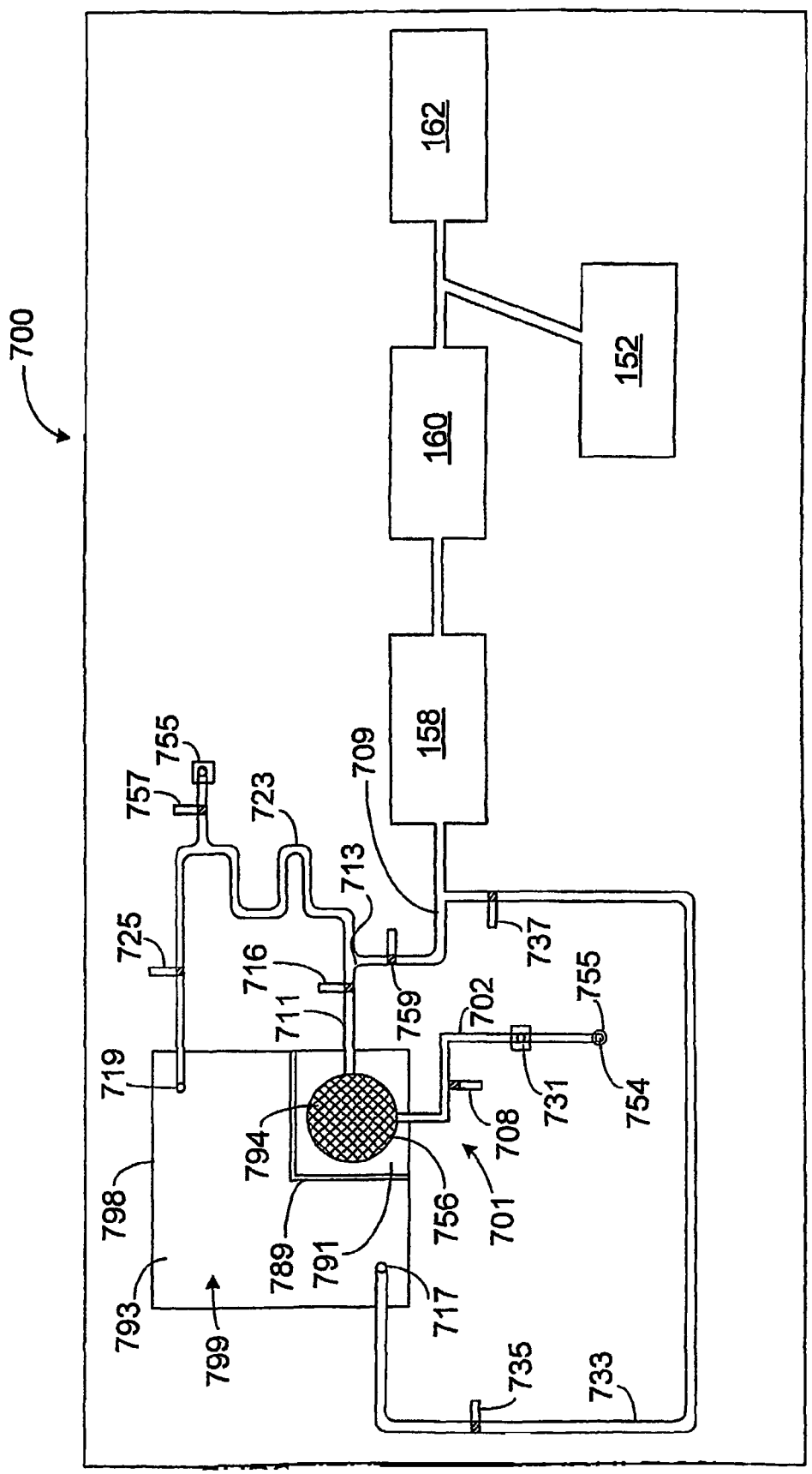
FIG. 7 is a top view of a fourth embodiment of a microfluidic device.

Referring to FIG. 7, a microfluidic device 700 receives an amount of a particle-containing fluidic sample and prepares an enriched sample including a greater abundance of the particles. The preparation of the enriched sample includes spatially separating particles of the particle-containing sample from fluid of the sample. Device 700 uses pressure created during the spatial separation to manipulate sample and/or reagent material, such as to move such materials about device 700. These and other aspects of device 700 are discussed below.

Device 700 includes a microfluidic network 701 including an input port 754, an enrichment region 756 in communication with input port 754 by a channel 702, and a reservoir 798 defining a chamber 799 to receive fluid from enrichment region 756. Channel 702, upstream of enrichment region 756, includes a valve 708 to selectively obstruct passage of material between input port 754 and enrichment region 756. Valve 708 may have features of valve 208 or other valves (or gates) discussed herein. Valve 708 has a normally open state that allows material to pass along channel 702.

Enrichment region 756 includes a retention member 794 to spatially separate particles of a particle-containing sample from fluid of the particle-containing sample. Retention member 794 allows fluid, e.g., gas and/or liquid, to pass therethrough and into reservoir 798 while retaining particles. Enrichment region 756 may have features of enrichment region 56 or other enrichment regions discussed herein. Retention member 794 may have features of retention member 94 or other retention members discussed herein.

Chamber 799 defines a first portion 791 and a second portion 793 separated by a liquid barrier, e.g., an internal wall 789, configured to allow gas to pass between portions 791, 793 but to prevent liquid from passing between these portions of chamber 799. A channel 711 extends downstream from first portion 791. A channel 723 extends downstream from an outlet 719 of second portion 793 and joins channel 711 at an intersection 713.

Channel 723 includes a gate 725 to selectively obstruct or allow passage between second portion 793 of chamber 799 and downstream portions of channel 723. Gate 725 may have features of gate 216 or other gates (or valves) discussed herein. Gate 725 has a normally closed state that obstructs passage. A vent 755 is in gaseous communication with channel 723. A valve 757, having a normally open state, is configured to selectively allow or obstruct passage of gas between channel 723 and vent 755.

Channel 711 includes a gate 716 and a gate 759 to selectively obstruct or allow passage between enrichment region 756 and downstream locations of microfluidic network 701. Gates 716 and 759 may have features of gate 216 or other gates (or valves) discussed herein. Gates 716 and 759 are typically configured to have a normally closed state that obstructs passage of material between enrichment region 756 and downstream locations of network 701. Downstream locations of network 701 typically include lysing module 158, DNA clean-up module 160, detection module 162, and reagent module 152.

Device 700 may be operated as follows. A particle-containing sample is introduced, such as by using a sample introduction device, e.g., a syringe, mated with a fitting 755 of input port 754. With valve 708 in the open state and gates 716,725 in the closed state, sample material passes along channel 702 into enrichment region 756. Pressure created by the sample introduction device drives fluid of the sample through retention member 794 and into first portion 791 of chamber 799 of reservoir 798. Entry of fluid into first portion 791 of chamber 799 increases the pressure within chamber 799. Retention member 794 retains particles of the sample within enrichment region 756.

Once a sufficient amount of sample material has been introduced, the enrichment region may be sealed to prevent pressure created within chamber 799 from being vented or driving material out of enrichment region 756. For example, valve 708 may be actuated to the closed state to prevent passage of material between input port 754 and enrichment region 756 along channel 702. With valve 708 and gates 716, 725 in the closed state, device 700 maintains the pressure within chamber 799.

To prepare an enriched sample, gate 716 is actuated to the open state thereby providing a passage for material to exit chamber 799. The relatively greater pressure within the chamber drives fluid therein through retention member 794 and into enrichment region 756. Thus, the fluid preferably passes through retention member 794 in an opposite direction from the fluid that entered chamber 799 through retention member 794.

Typically, only a subset of fluid that entered chamber 799 passes back through retention member 794. The amount of fluid, e.g., liquid, that passes into enrichment region 756 through retention member 794 is typically less than 50%, less than 10%, less than 2.5%, or less than 1% of the volume of fluid, e.g., liquid, introduced with the sample. For example the amount of fluid, e.g., liquid, that passes into enrichment region 756 through retention member 794 may be less than 50 microliters, less than 25 microliters, less than 15 microliters, less than 10 microliters, or less than 5 microliters. Thus, device 700 prepares an enriched particle-containing sample including particles of the particle-containing sample and a subset of the fluid that was originally introduced to device 700.

Typically, pressure within chamber 799 also drives the enriched particle-containing sample toward downstream portions of network 701. In some embodiments, a volume of the enriched particle-containing sample driven downstream is determined by a volume of a downstream portion of network 701. For example, with gates 725, 759 closed and upon actuating gate 716, pressure within chamber 799 drives at least a portion of the enriched particle sample along channel 711 and into channel 723 beyond intersection 713. Enriched sample is driven along channel 723 until a downstream terminus of enriched sample reaches vent 755 inhibiting further movement of the sample. The volume of the enriched sample is substantially determined by a volume of channel 723 intermediate vent 755 and gate 759.

Once sample has filled channel 723, gate 716 may be re-closed or a valve (not shown) located along channel 711, may be actuated to obstruct passage of material between channel 723 and enrichment region 756. Then, gates 725 and 759 are actuated. Opening gate 725 places intersection 713 between channels 711 and 723 in communication with second portion 793 of chamber 799 via outlet 719. With gate 725 open, pressure within chamber 799 drives material further downstream of intersection 713. For example, the pressure may drive material toward lysing module 158.

Chamber 799 of device 700 may include one or more additional output ports configured to allow pressure within chamber 799 to be used to manipulate and/or move sample, reagent, or other materials elsewhere within network 701. For example, outlet 717 communicates with channel 733 which itself intersects with channel 709 upstream of lysing region 158. A gate 735 selectively obstructs or allows passage of material between outlet 717 and channel 733. A gate 737 selectively obstructs or allows passage of material between channels 709 and 733. Upon preparation of a lysed sample, gates 735, 737 are opened whereupon pressure from chamber 799 moves the lysed sample downstream of lysing chamber 158.

Figure 8:
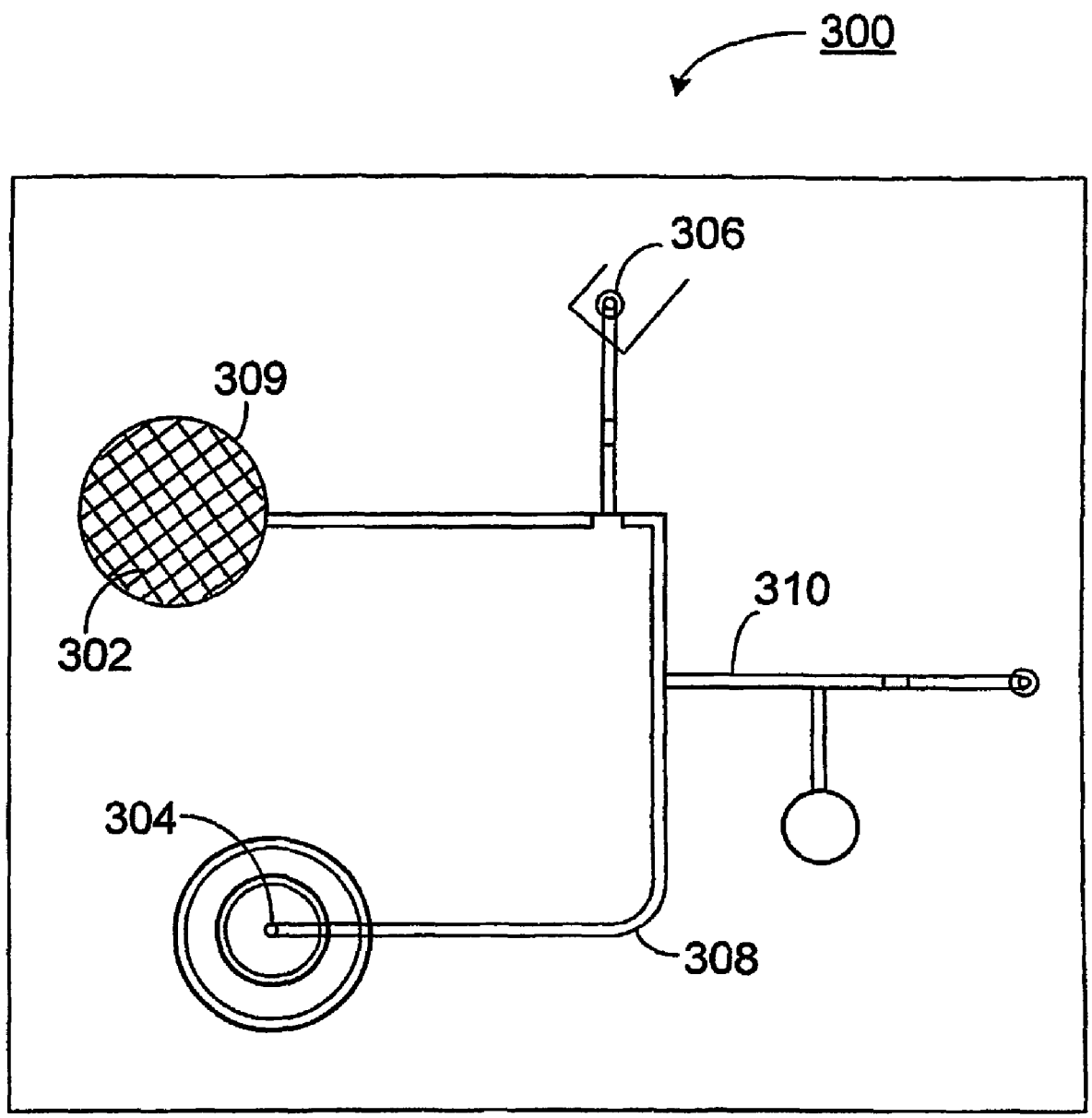
FIG. 8 is a top view of a fifth embodiment of a microfluidic device.

Referring to FIG. 8, a microfluidic device 300 includes a sample enrichment region 302, a port 304 for introducing sample material to device 300, a port 306 for the output of processed sample material, a channel 308 connecting the enrichment region 302 and, and a valve 310 for obstructing passage of material along channel 308 between enrichment region 302 and port 304.

In use, a given amount of sample material is introduced via port 304, which may be configured to mate with a standard syringe. The amount of sample introduced depends upon the analysis and may be, e.g., at least about 0.25 ml, at least about 0.5 ml, at least about 1 ml, and, e.g., less than about 5 ml, less than about 2.5 ml, or less than about 1.5 ml.

Sample material passes along channel 308 to enrichment region 302. The fluid travels into the concentration region (including a circular filter whose center is typically free and whose edge 309 is secured to the chip) and through the filter leaving the cells or other particles of interest behind at an internal surface of the filter. The waste fluid, may pool on top of the device, and can be discarded, assuming a thin meniscus of liquid remains on the top of the filter to prevent drying and to provide a reservoir from which to backflow. Once the cells are trapped by the filter, the user actuates the valve 310, thus obstructing the passage of material between port 304 and enrichment region 302. Then the tape is removed, and an external device, e.g., a pipette or syringe, is used to backflow some of the liquid of the sample back through the filter to re-entrain the cells. Typically, less than 25%, less than 10%, less than 5%, less than 2.5%, or less than 1% of the fluid introduced with the particles re-entrains the particles.

Microfluidic Device Including a Thermally Actuated Lysing Module

Figure 9A:
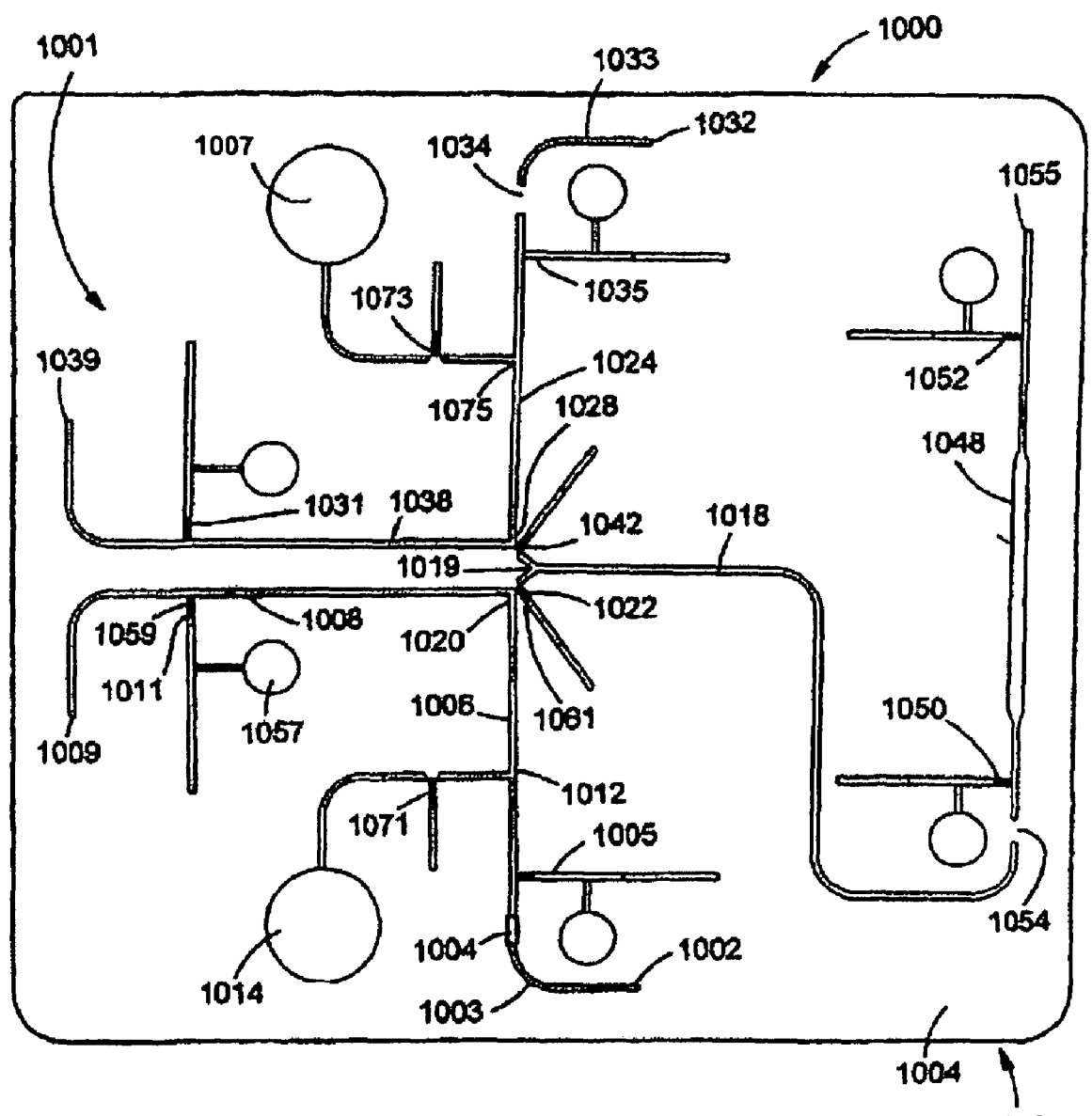
FIG. 9a is a top view of a sixth embodiment of a microfluidic device.

Referring to FIG. 9a, a microfluidic device 1000 includes a microfluidic network 1001 having a input port 1002 leading to a channel 1003 including a vent 1004 and a valve 1005, which has a normally open position but can be closed to obstruct passage of material between channel 1003 and a lysing region 1006 downstream of valve 1005. A downstream portion 1020 of lysing region 1006 joins a waste channel 1008, which leads to a waste port 1009. A valve 1011 selectively allows or obstructs passage of material along channel 1008 to waste port 1009. A gate 1022 selectively obstructs or allows passage of material downstream from lysing region 1006.

A thermopnuematic actuator 1014 generates a gas pressure sufficient to move material, e.g., a lysed sample, downstream from lysing region 1006 and into channel 1018. Actuator 1014 typically operates by generating an upstream pressure increase but device 1000 can be configured with an actuator that provides a downstream pressure decrease, e.g., a partial vacuum, to move material downstream from lysing region 1006. A gate 1071 selectively obstructs or allows passage of material between actuator 1014 and lysing chamber 1006.

Network 1001 includes a reagent input port 1032 leading to a channel 1033 including a vent 1034 and a valve 1035, which has a normally open position but can be closed to obstruct passage of material between channel 1033 and a reagent metering chamber 1024 downstream of valve 1035. A downstream portion 1028 of reagent metering chamber 1024 joins a waste channel 1038, which leads to a waste port 1039. A valve 1031 selectively allows or obstructs passage of material along channel 1038 to waste port 1039. A gate 1042 selectively obstructs or allows passage of material downstream from reagent metering chamber 1024.

A thermopnuematic actuator 1007 generates a gas pressure sufficient to move material, e.g., an amount of reagent, downstream from reagent metering chamber 1024 and into channel 1018. Actuator 1007 typically operates by generating an upstream pressure increase but network 1001 can be configured with an actuator that provides a downstream pressure decrease, e.g., a partial vacuum, to move material downstream from reagent metering region 1024. A gate 1073 selectively obstructs or allows passage of material between actuator 1007 and reagent metering region 1024.

With gates 1022, 1042 in the open state, downstream portion 1020 of lysing region 1006 and downstream portion 1028 of reagent metering chamber 1024 lead to an intersection 1019, which is the upstream terminus of a channel 1018. The channel 1018 leads to a reaction chamber 1048 having an upstream terminus defined by a valve 1050 and a downstream terminus defined by a valve 1052. Valves 1050, 1052 can be closed to prevent material from exiting reaction chamber 1048. A vent 1054 allows degassing, debubbling of material passing along channel 1018 into chamber 1048. A vent 1055 prevents pressure buildup from preventing material from entering chamber 1048.

Gates and valves of network 1001 are typically thermally actuated and may have features of other valves and gates discussed herein. For example, valve 1011 includes a mass of IRS 1059 and a pressure chamber 1057. Increasing a temperature of TRS 1059 and a pressure within chamber 1057 drives TRS 1059 into channel thereby obstructing the channel. Gate 1022 includes a mass of TRS 1061 that obstructs passage of material from lysing region 1006 to intersection 1019. Raising a temperature of TRS 1061 allows upstream pressure (or a downstream partial vacuum) to move material from lysing region into intersection 1019 and channel 1018.

Vents of network 1001 typically include a porous hydrophobic membrane as discussed for vents of other devices herein. The vents allow gas to escape network 1001 but inhibit or prevent liquid from escaping.

Device 1000 is typically configured to receive a cell-containing sample, lyse the cells to release intracellular material, combine the intracellular material with reagents, e.g., reagents suitable for PCR amplification and detection, deliver the combined reagents and intracellular material to the reaction chamber 1048, amplify DNA present in the intracellular material, and detect the presence or absence of a particular type of cell, e.g., group B strept, based upon the detected DNA.

Figure 9B:
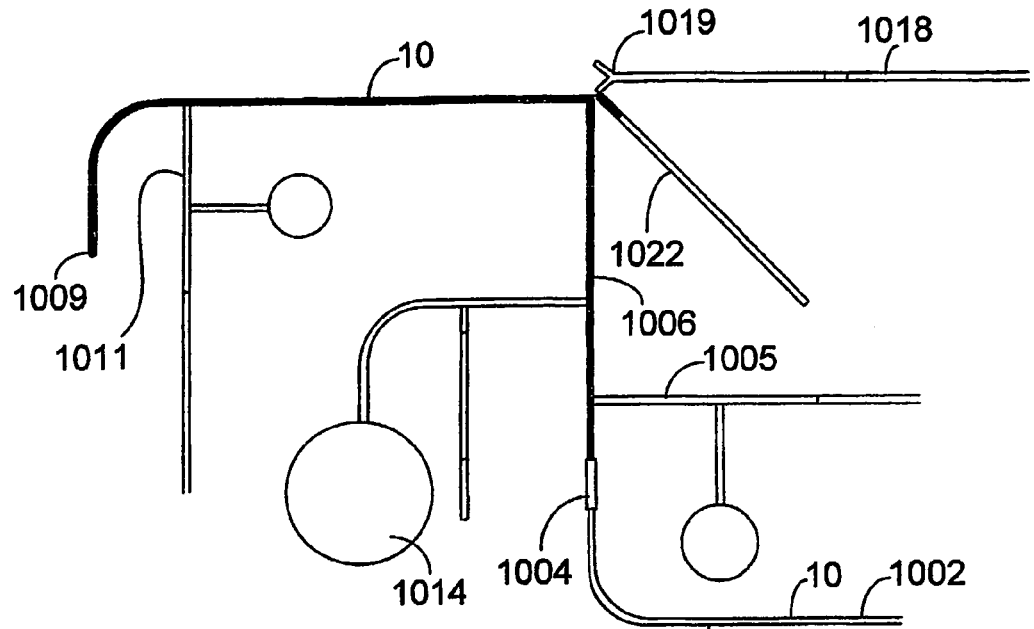
FIG. 9b is a close-up view of a portion of the microfluidic device of FIG. 9a, an amount of sample having been added.
Figure 9C:
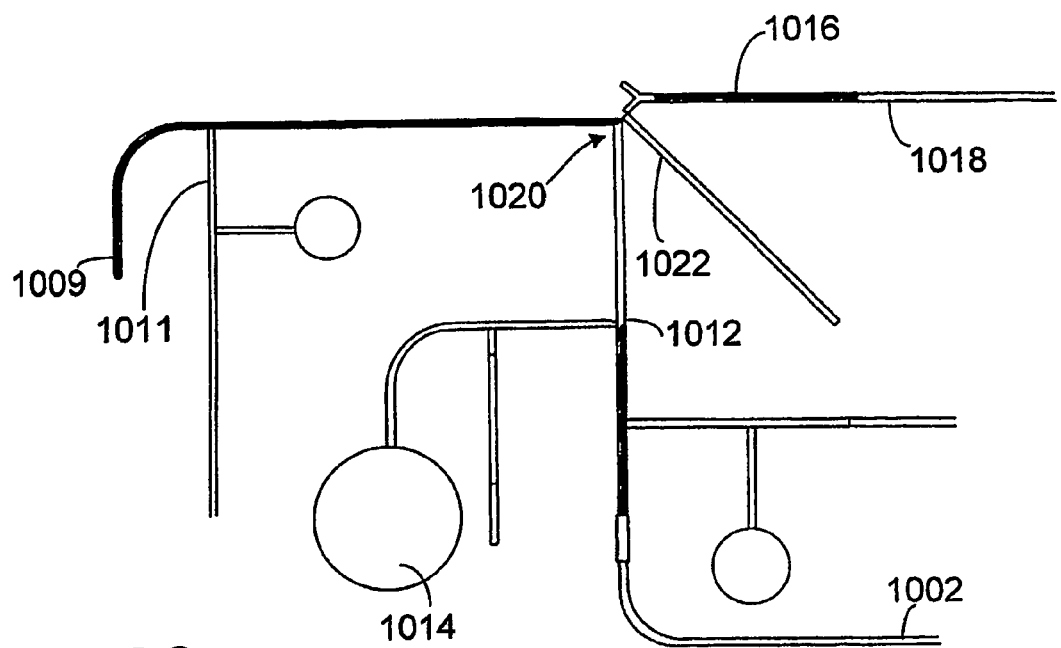
FIG. 9c is a close-up view of a portion of the microfluidic device of FIG. 9b, an amount of sample having been added and a microdroplet of the added sample moved downstream.

Referring to FIGS. 9b and 9c, exemplary operation of device 1000 includes introducing a volume of particle-containing sample into network 1001 via inlet 1002. Sample material moves along a channel 1003 toward lysing chamber 1006. Gas, such as air bubbles possibly introduced with the sample, are vented from the microfluidic network at vent 1004. Sample material enters and fills lysing chamber 1006. Gate 1022 is closed thereby preventing passage of sample downstream toward intersection 1019. Excess sample material travels along waste channel 1008 to a waste port 1009, which may provide passage to a waste chamber.

Even if excess sample is introduced, the volume remaining within the microfluidic network and the position occupied by the remaining volume is preferably determined by the volume of the respective channels and the position of any vents (FIG. 9b). For example, upon introduction of the sample, the vent 1004 prevents an upstream portion of the sample material from being positioned downstream of an upstream opening 1012 of lysing chamber 1006. Thus, lysing chamber 1006 is completely filled with sample material (FIG. 9b).

Reagent materials may be introduced to network 1001 via port 1032. Waste channel 1038 and waste port 1039 cooperate with reagent metering region 1024 to deliver an amount of reagent materials and position the reagent materials in the same way that waste channel 1008 and waste port 1009 cooperate with lysing chamber 1006 to deliver an amount of sample and position the sample. Reagent materials may also be stored on the device during manufacture as discussed elsewhere herein.

Within the sample introduced and present within lysing chamber 1006, valves 1011, 1005 are closed. Closure of valves 1011, 1005 isolates sample within lysing chamber 1006 from the atmosphere surrounding device 1000. By isolate, it is meant that sample material present within lysing chamber 1006 may be heated by an amount sufficient to lyse cells therein within without significant evaporation of liquid accompanying the cells. In one embodiment, for example, material within lysing chamber 1006 may be heated to as much as 93.degree. C., 95.degree. C., or 97.degree. C., for as long as 1 minute, 2 minutes, 3 minutes, or even 5 minutes without substantial loss of the liquid within the lysing chamber. In some embodiments, less than 20%, less than 10%, less than 5%, or less than 2.5% of the liquid present in the lysing chamber is lost. In some embodiments, lysing chamber 1006, like lysing chambers of other lysing modules disclosed herein, has a volume of less than 5 microliters, less than 1 microliter, less than 500 nl, less than 200 nl, less than 100 nl, less than 50 nl, e.g., less than 10 nl.

As discussed above, valves 1011, 1055 typically include a mass of TRS, e.g., wax such as parafin, that operates to obstruct or allow passage of material. In the closed state, it is the TRS that obstructs gas and heated liquid from exiting lysing chamber 1006 (or reaction chamber 1048 for valves 1050, 1052). Insome embodiments, the obstructing mass of TRS can have a volume of 250 nl or less, 125 nl or less, 75 nl or less, 50 nl or less, 25, nl or less, 10 nl or less, 2.5 nl or less, 1 nl or less, e.g., 750 pico liters or less. Some or all of the TRS can pass downstream as discussed above.

Sample in lysing chamber 1006 is locally heated for a specified amount of time at a specific temperature to break open the target cells to release intracellular contents which include genetic material such as DNA. Heating lysing chamber 1006 is typically localized to prevent perturbation of other components of device 1000. For example, if gates 1071, 1073 are thermally actuated gates, heat used to lyse cells within lysing chamber 1006 generally does not cause premature opening of these gates (or other gates of the device).

Turning to FIG. 9c, upon lysing cells of sample within chamber 1006, gates 1071, 1073, 1022, 1042 are opened. An open state of gate 1071 provides communication between actuator 1014 and an upstream portion of lysing chamber 1006 adjacent upstream opening 1012. An open state of gate 1022 provides communication between sample present within lysing chamber 1006 and downstream portions of the microfluidic network. An open state of gate 1073 provides communication between actuator 1007 and an upstream portion of reagent metering region 1024. An open state of gate 1042 provides communication between reagent present within metering region 1024 and downstream portions of the microfluidic network.

Pressure source 1022 in actuator 1014 is activated causing a pressure difference between the upstream and downstream portions of sample present within lysing chamber 1006. Typically, an upstream pressure increases relative to a downstream pressure, causing an amount of the sample to move downstream, for example to a downstream channel 1018 (FIG. 16e). Pressure source Actuator 1007 is activated causing a pressure difference between the upstream and downstream portions of reagent within region 1024. Typically, an upstream pressure increases relative to a downstream pressure, causing an amount of the sample to move downstream, for example to a downstream channel 1018, where the reagent mixes with the lysed contents of the sample.

The volume of sample moved downstream from the lysing chamber 1006 is typically known. In the embodiment shown, for example, the volume is determined by the volume of lysing chamber 1006 between upstream and downstream portions 1012, 1020 thereof. Valves 1057, 1005 may cooperate in preparation of a known amount of sample by closing alternative passages into which material present in lysing chamber 1006 might flow upon actuation of actuator 1014.

Referring back to FIG. 9a, device 1000 combines a known amount of reagent with sample material, preferably with sample 1016 including released cellular contents. The volume of reagent combined with the sample is determined by a volume of network 1001 intermediate an outlet 1075 of actuator 1007 and gate 1042. Sample and reagent material move along channel 1018 into reaction chamber 1048. Once reagents and sample material are present within chamber 1048, valves 1050, 1052 are closed. The sample reagent mixture within chamber 1048 is typically subjected to one or more heating and cooling steps, such as to amplify polynucleotides present in the sample reagent mixture.

Thermal energy may be provided to the mixture by heating elements integral with device 1000 and/or by heating elements separate from device 1000. For example, external heating elements may be associated with an operating station adapted to receive device 1000. When the device 1000 is received by the operating station, the heating elements are positioned to heat particular areas, for example, actuators, valves, gates, lysing chamber 1006, and reaction chamber 1048.

In the closed state, valves 1050, 1052 limit or prevent evaporation of the sample reagent mixture during reaction, for example, by isolating the sample reagent mixture from the surrounding atmosphere. In some embodiments, the sample reagent mixture may be heated to between about 90° C. and about 99.75° C., for example between about 92° C. and about 98° C., for example about 97° C., for at least about 2 minutes, for example between about 3 minutes and about 10 minutes with a loss of no more than about 10 percent by weight, for example, no more than about 5 percent, or no more than about 2.5 percent of the sample reagent mixture.

Device 1000 is typically a multilayer construction. In one embodiment, device 1000 includes a first, injection molded layer defining features such as channels, chambers, valves and gates of network 1001. A second layer, typically a flexible laminate, overlies the first layer to seal the network. In general, the flexible laminate has a thickness of less than 500 microns, such as less than 250 microns. The laminate also provides efficient transfer of thermal energy between heat sources adjacent an outer surface of the laminate and material present within the microfluidic network 1001.

In some embodiments, heat sources, e.g., resistive heaters, are located external to device 1000 but in thermal communication with the outer surface of the second layer. In another embodiment, heat sources are integrally formed with device 1000, for example, within the first, injection molded layer. Exemplary placement and operation of heat sources is discussed below and elsewhere herein.

Device 1000 may also include a third layer, which is preferably disposed adjacent a surface of the first layer that abuts the second layer. Thus, the second and third layers may sandwich the first layer therebetwen. The third layer may contact a surface of the first layer that includes only a subset, if any, of the components of the microfluidic network 1001. Tn some embodiments, however, access ports and vents provide passage between the microfluidic network 1001 and the opposed surface of the first layer. For example, access ports 1002, 1032 maybe configured to allow sample material to be introduced through the third layer and into the microfluidic network. The ports can be configured to mate with a sample introduction device, such as a syringe.

Waste ports 1009, 1039 can extend through the first and third layers to a reservoir into which excess sample and reagents introduced to the microfluidic network may be received and contained from spillage.

Vents 1004, 1034 and other vents of device 1000 can extend through the first and third layers. Typically, the vents include a hydrophobic filter that allows passage of gases but inhibits passage of cells or aqueous liquids.

Network 1001 can also include hydrophobic patches, such as a coating within a portion of the microfluidic network, to assist in defining a predetermined volume of materials and positioning the materials relative to components of the microfluidic network as discussed elsewhere herein.

Valves and Gates for Fluid Control

As discussed elsewhere herein, microfluidic devices include gates and valves to selectively obstruct or allow passage of material within microfluidic networks. For example, gates and/or valves can prevent the evaporation of liquid from a sample subjected to heating such as for lysing cells or amplifying DNA. As discussed herein, gates typically include a mass of TRS, which, in the closed state, obstructs passage of material along a channel. Upon opening the gate, at least a portion of the TRS typically enters a downstream channel of the device. Valves typically operate by introducing a mass of TRS into an open channel to obstruct the channel. An exemplary device for use as a fluid control element, e.g., a gate or valve, is discussed below.

Figure 10:
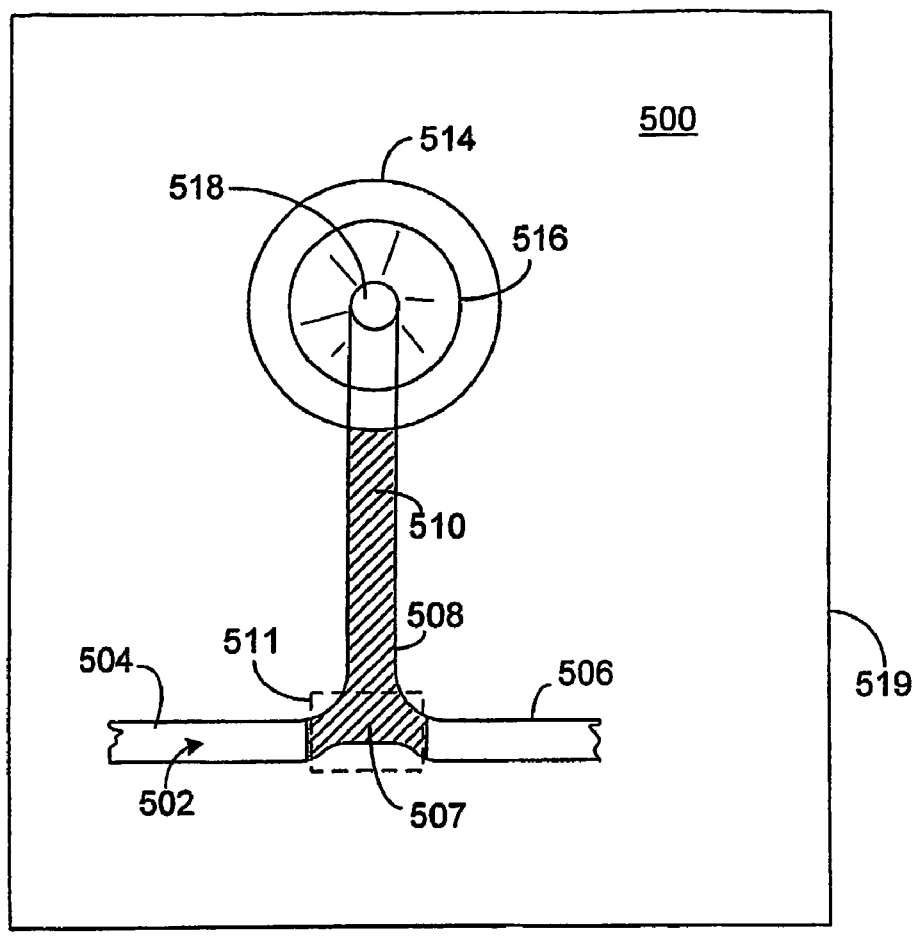
FIG. 10 is a top view of a device for alternatively obstructing and permitting passage of material within a microfabricated channel.
Figure 11:
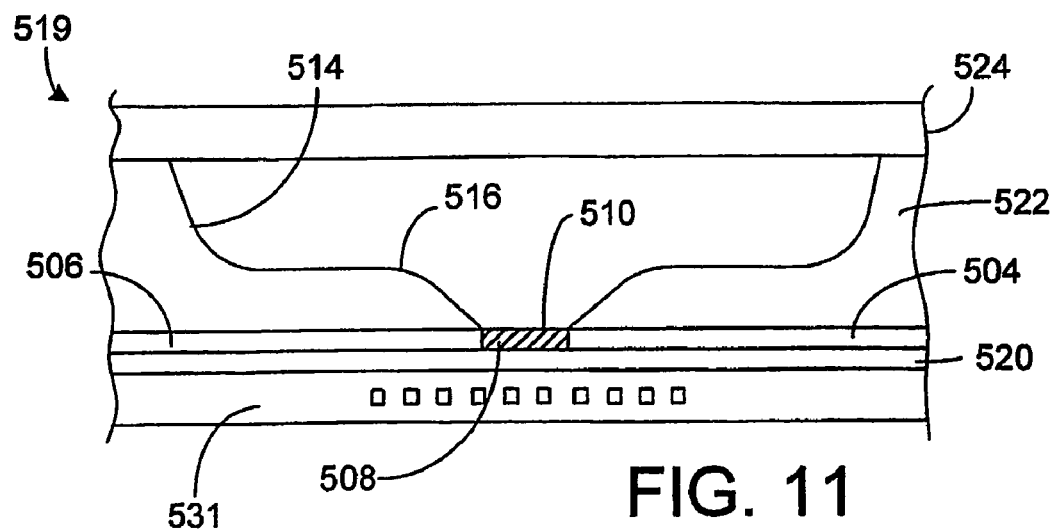
FIG. 11 is a cross section looking down a side channel of the device of FIG. 10.
Figure 12:
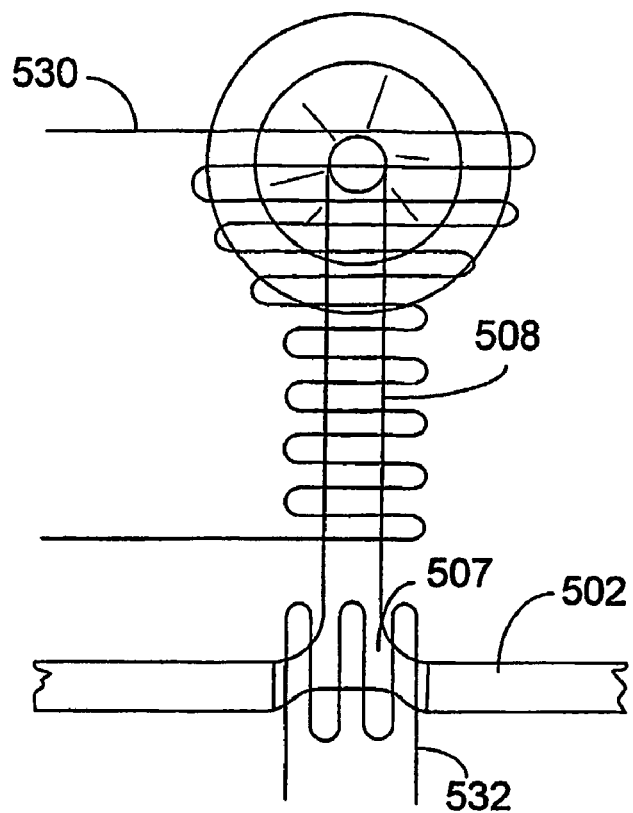
FIG. 12 shows the device of FIG. 10 with a heat source positioned to actuate the device.

Referring to FIGS. 10-12, a device 500 selectively obstructs or allows passage between an upstream portion 504 and a downstream portion 506 of a channel 502 of a microfluidic device. For clarity, other components of the microfluidic device are not illustrated in FIGS. 10-12.

Device 500 can be operated as a normally closed device, e.g., a gate, which opens upon actuation to allow passage between upstream and downstream portions 504, 506. Device 500 can also be operated as a normally open device, e.g., a valve, which closes upon actuation to obstruct passage between upstream and downstream portions 504, 506. Thus, device 500 combines features of both gates and valves, as discussed herein, and may be used in the place of any gate or valve of any device disclosed herein.

Device 500 is typically implemented as a component of a microfluidic network fabricated within a substrate 519 having a first layer, 520, a second layer 522, and a third layer 524. The microfluidic network is substantially defined between first and second layers 520, 522. In use, device 500 is located in thermal contact with a heat source, which is typically fabricated on or within a substrate 531. Substrate 531 may or may not be integral with the substrate 519.

Device 500 includes a side channel 508, which intersects channel 502 at a gate region 507 (within box 511) thereof, and a mass of TRS 510 present in at least side channel 508. When TRS 510 extends into gate region 507, channel 502 is obstructed. When TRS does not fill gate region 507, passage between upstream and downstream portions 504, 506 of channel 502 is allowed. In the closed state, a length of TRS 510 along channel 502 is at least about 1.5 times greater, e.g., at least about 2 times greater than a width of channel 502.

Channel 502 is preferably from about 25 to about 400 microns wide and from about 10 to about 300 microns deep. Channel 502 has a depth that is typically from about 2 to 3 times a depth of the gate region 507, which may be, e.g., about 5 to about 200 microns deep. Side channel 508 may be from about 0.75 to about 4 millimeters long and have a width of from about 50 to about 400 microns.

Side channel 508 includes an end 518 that connects to a hole 516 that connects in turn to a chamber 514. Hole 516 is at least about 100 microns, at least about 150 microns, e.g., at least about 400 microns in diameter where it joins chamber 514, which may be at least about 750 microns, at least about 1000 microns, e.g., at least about 1,400 microns in diameter and at least about 150 microns, at least about 250 microns, e.g., at least about 350 microns deep. Chamber 514 and hole 516 may have non-circular shapes. An end of side channel 508 at hole 516 can be rounded with a radius of about 10 microns to about 200 microns, e.g., about 150 microns.

Chamber 514 and channels 502, 508 are typically located on opposite sides of layer 522, which allows for a greater density of channels. For example, side channel 508 and channel 502 are typically defined between layers 522 and 520 whereas chamber 514 is typically defined between layers 522 and 524. A surface of layer 524 may define a wall of chamber 514 that is larger than a surface of chamber 514 defined by layer 520. A surface of layer 520 may define at least one wall of channel 502 and side channel 508. Typically, a surface of layer 524 does not define a wall of channel 508.

Referring also to FIG. 12, device 500 includes first and second heat sources 530, 532. First heat source 530 raises a temperature of material present within chamber 514 and hole 516 and at least a portion of side channel 508. For example, heat source 530 may heat material present in chamber 514 by an amount sufficient to raise a pressure within chamber 514 by at least about 10%, at least about 20%, at least about 35%, e.g., at least about 50%. Heat source 530 also raises a temperature of TRS present within hole 516 and at least a portion of side channel 508 to the second temperature at which the TRS is more mobile. Second heat source 532 is configured to raise a temperature of TRS present within gate region 507 to the second, temperature. The increased pressure within chamber 514 may move the entire mass 510 of TRS toward channel 502.

In some embodiments, however, device 500 includes a single source of heat that both raises a pressure within chamber 514 and raises the temperature of TRS 510. Using a single heat source reduces the number of electrical connections required to operate device 500.

Typically, channels 502, 508 hole 516, and chamber 514 are fabricated by injection molding layer 522. Layers 520 and 522 are typically mated to layer 522 by lamination. Layer 524 typically covers the entire open portion of chamber 514 and is preferably sufficiently rigid (or is provided with additional support elements) to withstand flexing during pressurization of chamber 514.

In a typical fabrication method, layer 522 is fabricated with a microfluidic network including channel 502, side channel 508, hole 516, and chamber 514. Layers 520 and 522 are mated. With the application of heat, TRS is loaded through hole 516. Capillary action draws the TRS into gate region 507 thereby obstructing channel 502. Layer 524 is mated to layer 522.

Device 500 may be opened by actuating heater 532 and applying pressure within channel 502 to move TRS present in the gate region. Device 500 may be closed again by actuating heater 530 to pressurize chamber 514 and heat TRS 510 present in hole 516 and side channel 508 to the second more mobile temperature. The pressure within chamber 514 moves TRS 510 into gate region 507. Heater 532 may also be actuated to close device 500.

Microfluidic Device Configured for Mechanically-Generated Vacuum Sample Introduction Typical methods for introducing sample to microfluidic devices involve user interaction with five separate objects. For example, using a tube of transfer buffer, a syringe, a needle or non-piercing needle substitute, a sample-laden swab, and a microfluidic device, the user might elute the sample off of the swab and into the tube of transfer buffer. After elution, the sample-laden buffer is drawn into the syringe through the needle, the needle is removed, and the contents of the syringe are injected onto the microfluidic device, such as through an input port thereof.

Figure 13:
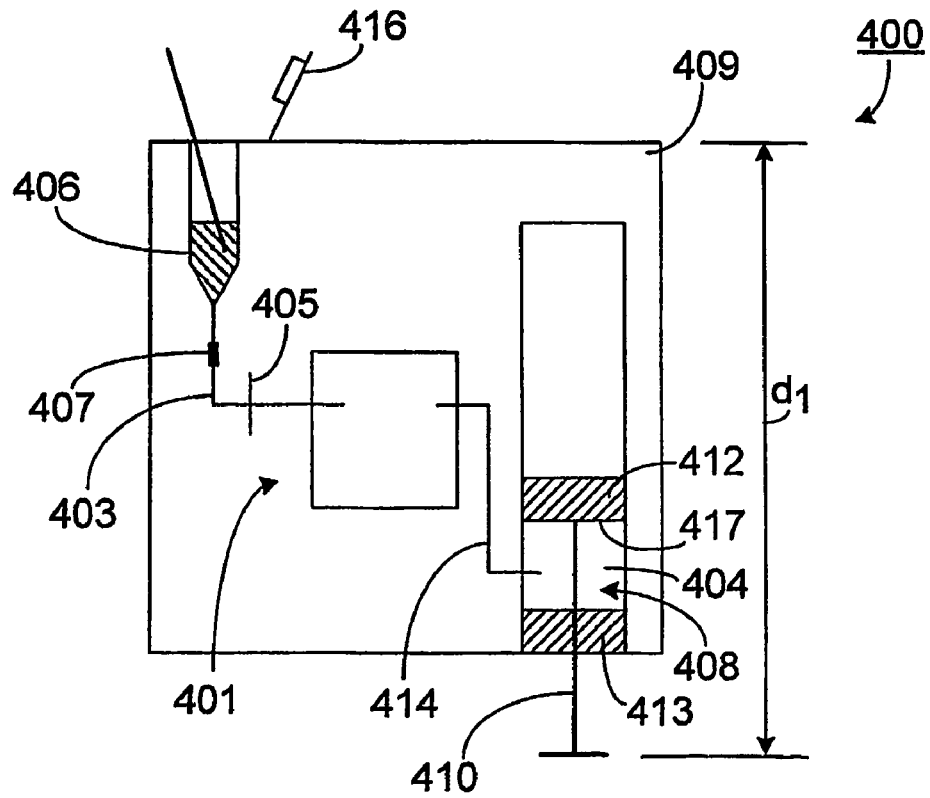
FIG. 13 is a top view of a seventh embodiment of a microfluidic device, the device having an integral mechanical vacuum generator.

Referring to FIG. 13, a microfluidic device 400 reduces the number of objects that must be manipulated to prepare and load a sample. Device 400 includes a microfluidic network 401, a mechanical vacuum generator 404, and a buffer reservoir 406. Network 401 can be defined within layers of a substrate and include various modules, chambers, channels, and components, as discussed elsewhere herein.

Buffer reservoir 406 is typically pre-loaded with buffer by the manufacturer but can be loaded with buffer by the user. When pre-loaded, reservoir 406 is sealed to prevent evaporation of preloaded buffer and or leakage of the buffer into network 401. For example, a cap 416 seals buffer reservoir 406. In use, a user deposits a portion of a sample swab into reservoir 406. For example, a user might break off the tip of a sample swab within the reservoir. Cap 416 is secured to seal the buffer and swab within reservoir 406. Thus, the user may agitate the entire device 400 without leakage.

Microfluidic network 401 may include any combination of features of microfluidic networks 51, 110, 201, and 701 discussed above. Buffer reservoir 406 communicates with network 401 via a channel 403, which may include a filter 405 configured to retain larger undesired particles, and a vent 407 configured to allow gas to escape from channel 403.

Vacuum generator 404 includes a chamber 408 defined between first and second gaskets 412, 413 of a plunger 410. Chamber 408 is in communication with network 401 via a channel 414. Plunger 410 and gasket 412 slide within substrate 409 expanding the size of chamber 408 between a surface 417 of gasket 412 and gasket 413. Plunger 410 and gasket 412 typically slide along a plunger axis, which is substantially parallel to a plane of network 401 and substrate 409. Vacuum generator 404 thus generates a reduced pressure within chamber 408 to manipulate material, e.g., sample material and/or reagent material, therein. In a preferred embodiment, the reduced pressure assists the introduction of sample material to device 400. In another embodiment, the reduced pressure assists the preparation of an enriched sample.

As plunger 410 is depressed (moved further into substrate 409), the size of chamber 408 increases. Preferably, channel 414 provides the only passage for gas to enter chamber 408. Thus, depressing plunger 410 creates a pressure differential between chamber 408 and network 401 urging material downstream within network 401 and toward chamber 408. The actuation of plunger 410 to create the at least partial vacuum typically decreases a dimension d, of device 400. Chamber 408 and gaskets 412, 413 typically prevent leakage of material that might be drawn into chamber 408.

Device 400 may be operated as follows. A user obtains a swab including sample material, e.g., cells or other particulates. The swab is contacted with buffer present in buffer reservoir 406, such as by agitating the swab within the reservoir. Cap 416 is then be secured. Plunger 410 is depressed thereby expanding the volume of chamber 404 and decreasing the pressure therein. Plunger 410 is actuated by the user, upon placing device 400 into an instrument configured to operate device 400, or by a device configured to operate device 400.

The decreased pressure (partial vacuum) resulting from plunger 410 actuation draws material from buffer reservoir 406 further into microfluidic network. For example, sample/buffer material may be drawn past vent 407 and through filter 405. In one embodiment, network 401 includes an enrichment region as described for networks 51 and 201 and the actuation of plunger 410 draws sample into or out of the enrichment region.

Device 400 may also include a mechanical seal (not shown) that is ruptured or otherwise opened before or upon actuation of the mechanical vacuum generator 404. Rupture of the seal typically releases reagents, whether dried, liquid or both, that can mix with sample introduced to the device. In some embodiments, device 400 includes a hydrophobic membrane (not shown) having a bubble point attained by actuation of the mechanical vacuum generator. In this case, downstream components of network 401 may be sealed from the surrounding environment to prevent evaporation through the membrane.

Microfluidic Device Fabrication

Typical microfluidic devices include at least first and second substrates. In general, a first one of the substrates includes an injection molded polymer having a first surface that defines channels, chambers, valves, gates and other structures of a microfluidic network. The first substrate is typically rigid enough to allow the device to be manipulated by hand. The second substrate is generally a flexible laminate that overlies the first surface of the first surface and seals the microfluidic network. In some embodiments, a third substrate, e.g., a second flexible laminate, overlies the second surface of the first substrate. Passages defining ports and vents extend through the first and third substrate to allow fluid to be input and withdrawn from the microfluidic network and to allow gas and bubbles to vent from the network.

An exemplary method for fabricated microfluidic devices includes (a) providing a first substrate, (b) fabricating components, e.g., channels, chambers, and gas chambers, of a microfluidic network in a surface of the first substrate and (c) mating a second substrate with the first substrate, which preferably completes and seals the microfluidic network with the exception of vents, input ports, output ports and other components desired that may be in communication with the environment surrounding the microfluidic network.

Steps may be combined. For example, an injection molding step may both provide a substrate while also fabricating various components of a microfluidic network.

A preferred method for mating substrates includes lamination. The first substrate is cleaned, such as with a surfactant and water and then dried. The surface to be mated with the second substrate can be subjected to a corona discharge treatment to increase the surface energy of the first surface. A standard coronal discharge gun may be used.

The second substrate is mated with the first surface of the first substrate. The second substrate is preferably a flexible polymer, such as a polymeric laminate, e.g., a high clarity LDPE tape available from American Biltrite, Inc. A layer of adhesive, e.g., a pressure sensitive adhesive of the laminate, is generally placed between the first surface of the first surface and the second substrate. The mated first and second substrates are secured by the application of pressure and heat such as by using a laminator, e.g., a ModuLam 130 laminator available from Think & Tinker, LTD. A typical lamination temperature is about 110° C. at ⅚ of maximum velocity for the ModuLam 130 laminator.

Returning to FIGS. 4 and 5 as an example, device 200 includes a layer 251 of polymer substrate, e.g., a cyclic olefin polymer such as Ticona Topas 5013. Channels and other features of network 201 are fabricated by injection molding of the polymer substrate. The channels and other features are covered using a polymer layer 253, e.g., ABI Prism well-plate tape. Typically, polymer layer 253 is disposed beneath layer 251.

TRS of valves and gates is loaded. Retention member 94 and vent 206 are positioned. Pitting 232, reservoir 234, and retention member support 236 are positioned as part of a layer 255, which may be secured, e.g., using adhesive sealed or heat staking, to an upper surface of layer 251. The top of reservoir 234 is sealed using a hydrophobic membrane (not shown) similar to that used for vent 206. Exemplary methods for mating layers of microfluidic devices of the invention are discussed below. Microfluidic devices of the present invention are preferably at least substantially planar. Microfluidic networks of the present invention may include a plurality of features that define at least one plane.

Microfluidic devices in accordance with the present invention generally include at least a first substrate defining, on at least a first surface thereof, elements of a microfluidic network and a second substrate, mated with the first surface of the first surface to seal at least some portions of the microfluidic network. The first substrate can also include, on a second side thereof, elements of the microfluidic network.

Where the second side of the first substrate contains elements of the microfluidic network, a third substrate can be mated thereto to seal at least some portions of the network. Elements of the microfluidic network can include channels, actuators, pressure chambers, reaction chambers, detection chambers, enrichment zones, access ports, waste reservoirs and the like.

Substrates defining elements of microfluidic networks can be formed of any suitable material, such as silicon, quartz, glass, and polymeric materials, e.g., a cyclic olefin. The substrate can be homogenous or formed of one or more elements bonded together, such as a silicon substrate having a substrate bonded thereto, e.g., a quartz cover. At least one of the substrate and cover are micromachined with system features, including the valves, passages, channels, and heaters. Micromachining includes fabrication techniques, such as photolithography followed by chemical etching, laser ablation, direct imprinting, stereo lithography, and injection molding. A preferred fabrication technique includes injection molding a substrate using a machined master. Surfaces of channels and other injection-molded features may be tapered for ease of molding.

A preferred method for mating substrates includes lamination. The lamination process can include providing a first substrate including elements of a microfluidic network. The first substrate is preferably a polymeric substrate formed by injection molding. The first substrate is cleaned, such as with a surfactant and water. The first substrate is dried and the surface to be mated with the second substrate is subjected to a corona discharge treatment, such as to increase the surface energy of the first surface. A standard coronal discharge gun may be used.

The second substrate is mated with the first surface of the first substrate. The second substrate is preferably a flexible polymer, such as a polymeric laminate, e.g., a high clarity LDPE tape available from American Biltrite, Inc. A layer of adhesive is preferably positioned between the first surface of the first surface and the second substrate. For example, the surface of the second substrate to be mated with the first substrate can include a layer of pressure sensitive adhesive. The mated first and second substrates are secured preferably by the application of pressure and heat such as by using a laminator, e.g., a ModuLam 130 laminator available from Think & Tinker, LID. A typical lamination temperature is about 110° C. at ⅝ of maximum velocity for the ModuLam 130 laminator.

In some embodiments, the microfluidic device can include a third substrate mated with a second surface of the first substrate, the second surface opposing the first surface of the first substrate. The third substrate can include three dimensional features such as waste reservoirs, access ports, and the like. The third substrate and the first substrate can be mated using adhesive, adhesive laminate, heat staking, and the like.

EXAMPLES

Example 1

Bench Top Thermal Lysis

Two microliters of GBS culture at concentrations of about 100 cells/μl were lysed in the capillary tubes of a LightCycler at 97° C. for 0, 1, 2, 3, 4 and 5 min. After lysis, PCR (final volume: 7 μl) was performed in the same capillary tubes with GBS specific primers and probes. Purified genomic DNA from a commercial kit having from 10 to 10,000 copies was used to prepare standards for quantification. The amplication results indicate that as little as 1 min was sufficient to lyse the GBS cells.

Example 2

Lysis on Microfluidic Device

A microfluidic device including an epoxy-based substrate defining a 500 nl lysing chamber covered by a glass coverslip was prepared. About 500 nl of the GBS of Example 1 was loaded into the lysing chamber. The input port was sealed with an adhesive polymer. The chip was placed on a heater and lysed at 97° C. for 2 mm. The sample was retrieved by pipette and the volume of sample was brought up to 10. mu·l with TE buffer (pH 8.0). About 2 μl of this diluted sample was subjected to PCR. The experiment was repeated several times. The PCR amplification results demonstrate that a time of 2 min was sufficient to lyse the cells.

Injection molded microfluidic devices each having a lysis channel were prepared. The devices included two tapered holes at each end of a lysis channel, thereby allowing easy loading and retrieval of samples. The lysis channel was sealed with a laminate allowing efficient heat conduction and increasing the speed of device assembly.

Cultured GBS cells were diluted to a concentration of about 5,000 cells per μl in TE buffer and loaded into the lysis chambers of the devices. The lysis chambers had a volume of about 1 μl. The devices were heated to 97° C. for 0, 0.5, 1, 2, or 3 minutes. PCR amplification results indicated that lysis was essentially complete within 1 minute.

Example 3

Clinical Testing

Approximately 2 ml of GBS swab samples were submitted to the microbiology of a University Hospital for culturing. Samples of GBS having a volume of about 0.5 ml were prepared and stored at 4° C. for less than 24 hours. A code was assigned to each sample so the identity of the individual could not be determined. Samples were spun down in a centrifuge at 14 kRPM for about 2 min and resuspended in 0.5 ml TE with 0.02% SDS. The samples were then passed through a 3 μm Versapor Acrodisc syringe filter (Pall Gelman Laboratory) and spun down again. After centrifugation, the cells were resuspended in 1 μl of 0.02% SDS in TE buffer. The entire sample was loaded into a lysis chamber of a microfluidic device and sealed with laminate. The devices were heated to 97° C. for 3 min to lyse the cells. Samples were retrieved with a pipette and the volume of the samples was brought up to 5 μl. A 1 μl aliquot of the diluted samples was used for PCR with GBS specific primers and a GBS specific Taqman probe in a LightCycler. The clinical sensitivity: 83%; clinical specificity 91%, positive predictive value 65% and negative predictive value: 96%.

GBS samples as described above were combined with about 1 ml of Triton-X-1000 buffer and filtered through a polycarbonate filter (Poretics). The samples were lysed at 97° C. for 3 min to lyse the cells. The clinical sensitivity was 91%. The clinical specificity was 91%. The positive predictive value was 69% and the negative predictive value was 98%.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A microfluidic device comprising a microfluidic network, the device comprising:
   an input port for receiving a particle-containing liquidic sample;
   a retention member in communication with the input port and configured to spatially separate particles of the particle-containing liquidic sample from a first liquidic portion of the particle-containing liquidic sample;
   a reservoir in communication with the retention member and configured to receive at least some of the first liquidic portion separated from the particles, wherein a pressure within the reservoir increases upon receiving the first liquidic portion; and
   a gate configured to open a channel downstream of the reservoir thereby decreasing the pressure within the reservoir so that at least some of the separated particles recombine with a subset of the first liquidic portion separated from the particles.

2. The microfluidic device of claim 1, wherein a ratio of a volume of the subset of the first liquidic portion to a volume of the first liquidic portion is at least 1%.

3. The microfluidic device of claim 1, wherein a ratio of a volume of the subset of the first liquidic portion to a volume of the first liquidic portion is less than 25%.

4. The microfluidic device of claim 1, wherein the retention member is a filter.

5. A microfluidic device for processing a particle-containing liquid sample, including:
   an enrichment region, including:
      a retention member;
      a reservoir in communication with the retention member configured so that a first liquidic portion of a particle-containing liquid sample received therein enters the reservoir along an entry path including a first surface of the retention member, and particles of the particle-containing liquid sample are thereby retained by the retention member; and
      a gate having an open configuration wherein a subset of the first liquidic portion exits the reservoir along an exit path including the first surface of the retention member, wherein the entry path is substantially opposite the exit path.

* * * * *